United States Patent
Schneiderman

(10) Patent No.: US 10,105,469 B2
(45) Date of Patent: Oct. 23, 2018

(54) COMPOSITION-OF-MATTER AND METHOD FOR TREATING CARDIOVASCULAR DISORDERS

(71) Applicant: Jacob Schneiderman, Kiryat Ono (IL)

(72) Inventor: Jacob Schneiderman, Kiryat Ono (IL)

(*) Notice: Subject to any disclaimer, the term of this patent is extended or adjusted under 35 U.S.C. 154(b) by 158 days.

(21) Appl. No.: 14/730,282

(22) Filed: Jun. 4, 2015

(65) Prior Publication Data

US 2016/0250294 A1 Sep. 1, 2016

Related U.S. Application Data

(60) Provisional application No. 62/120,966, filed on Feb. 26, 2015.

(51) Int. Cl.

| | |
|---|---|
| *A61K 38/22* | (2006.01) |
| *A61K 38/00* | (2006.01) |
| *A61K 38/16* | (2006.01) |
| *A61L 31/16* | (2006.01) |
| *A61L 27/54* | (2006.01) |
| *A61L 27/58* | (2006.01) |
| *A61L 27/22* | (2006.01) |
| *A61L 31/14* | (2006.01) |
| *A61L 31/06* | (2006.01) |
| *A61L 31/04* | (2006.01) |
| *A61L 31/08* | (2006.01) |
| *A61L 27/18* | (2006.01) |
| *A61K 9/00* | (2006.01) |
| *A61K 9/70* | (2006.01) |
| *A61K 47/34* | (2017.01) |
| *A61K 9/06* | (2006.01) |

(52) U.S. Cl.
CPC .......... *A61L 31/16* (2013.01); *A61K 38/2264* (2013.01); *A61L 27/18* (2013.01); *A61L 27/227* (2013.01); *A61L 27/54* (2013.01); *A61L 27/58* (2013.01); *A61L 31/047* (2013.01); *A61L 31/06* (2013.01); *A61L 31/08* (2013.01); *A61L 31/148* (2013.01); *A61K 9/0019* (2013.01); *A61K 9/06* (2013.01); *A61K 9/7007* (2013.01); *A61K 47/34* (2013.01); *A61L 2300/43* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 7,807,154 B2* | 10/2010 | Strasburger | C07K 16/2869 424/130.1 |
| 8,969,292 B2* | 3/2015 | Gertler | A61K 38/22 514/21.2 |
| 2002/0090388 A1 | 7/2002 | Humes et al. | |
| 2007/0129790 A1* | 6/2007 | Peng | A61L 24/0015 623/1.42 |
| 2009/0274739 A1 | 11/2009 | Marks et al. | |
| 2014/0336750 A1 | 11/2014 | Mazer et al. | |

FOREIGN PATENT DOCUMENTS

WO 2011163669 A2 12/2011

OTHER PUBLICATIONS

De Rosa et al. 2007. Immunity 26:241-255.*
Tao et al. 2013. Art. Thromb Vasc Biol. 33:311-320.*
Purdam, et al. 2008. Am. J. Physio. Heart Circ Physiol. 295:H441-H446.*
Seif-Naraghi et al. 2013. Science Transl. Med. 5:173ra25.*
Cornelia Amalinei, Irina-Draga Căruntu. "Etiology and Pathogenesis of Aortic Aneurysm", Aortic Aneurysm—Recent Advances, Associate Prof. Cornelia Amalinei (Ed.). Chapter 1, pp. 1-40. Published: Apr. 10, 2013 http://dx.doi.org/10.5772/56093.
Jacob Schneiderman et al., (2008). Leptin receptor is elevated in carotid plaques from neurologically symptomatic patients and positively correlated with augmented macrophage density. Journal of Vascular Surgery, vol. 48, No. 5, Nov. 2008. pp. 1146-1155.
Jacob Schneiderman et al,. (2012). "Leptin Locally Synthesized in Carotid Atherosclerotic Plaques Could Be Associated With Lesion Instability and Cerebral Emboli".Journal of the American Heart Association, originally published on Sep. 4, 2012. pp. 1-11. http://jaha.ahajournals.org/content/1/5/e001727.

\* cited by examiner

*Primary Examiner* — Shulamith H Shafer
(74) *Attorney, Agent, or Firm* — Soroker Agmon Nordman

(57) ABSTRACT

A composition-of-matter for treating cardiovascular disorders and a method of using same are provided. The composition-of-matter includes a leptin antagonist and a carrier configured for localized release of the leptin antagonist.

12 Claims, 26 Drawing Sheets

Specification includes a Sequence Listing.

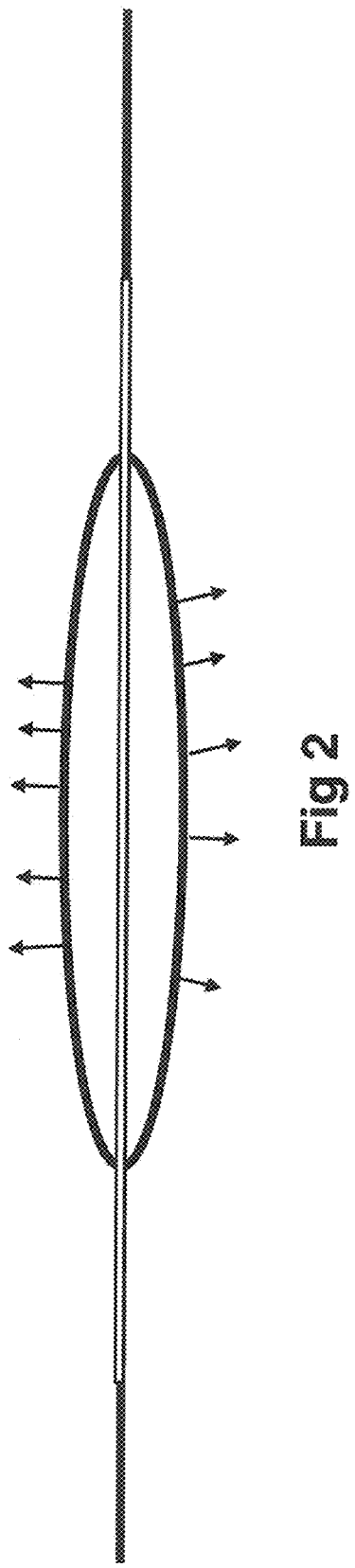

Leptin & Leptin Receptor in Human Normal Aortic Valve

SEQUENCE LISTING

```
<160> NUMBER OF SEQ ID NOS: 3

<210> SEQ ID NO 1
<211> LENGTH: 147
<212> TYPE: PRT
<213> ORGANISM: Artificial Sequence
<220> FEATURE:
<223> OTHER INFORMATION: synthetic

<400> SEQUENCE: 1

Ala Val Pro Ile Gln Lys Val Gln Asp Asp Thr Lys Thr Leu Ile Lys
1               5                   10                  15

Thr Ile Val Thr Arg Ile Asn Leu Ile Ser His Thr Gln Ser Val Ser
            20                  25                  30

Ser Lys Gln Lys Val Thr Gly Ala Ala Ala Ile Pro Gly Leu His Pro
        35                  40                  45

Ile Leu Thr Leu Ser Lys Met Asp Gln Thr Leu Ala Val Tyr Gln Gln
```

```
                    50                  55                  60
Ile Leu Thr Ser Met Pro Ser Gln Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
        130                 135                 140

Pro Gly Cys
145

<210> SEQ ID NO 2
<211> LENGTH: 147
<212> TYPE: PRT
<213> ORGANISM: Homo sapiens

<400> SEQUENCE: 2

Ala Val Pro Ile Gln Lys Val Gln Asp Asp Thr Lys Thr Leu Ile Lys
  1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
 50                  55                  60

Ile Leu Thr Ser Met Pro Ser Gln Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
        130                 135                 140

Pro Gly Cys
145

<210> SEQ ID NO 3
<211> LENGTH: 147
<212> TYPE: PRT
<213> ORGANISM: Artificial Sequence
<220> FEATURE:
<223> OTHER INFORMATION: synthetic

<400> SEQUENCE: 3

Ala Val Pro Ile Gln Lys Val Gln Asp Asp Thr Lys Thr Leu Ile Lys
  1               5                  10                  15

Thr Leu Val Thr Arg Ile Asn Leu Ile Ser His Thr Gln Ser Val Ser
                 20                  25                  30

Ala Lys Gln Arg Val Thr Gly Ala Ala Ala Ile Pro Gly Leu His Pro
            35                  40                  45

Ile Leu Ser Leu Ser Lys Met Asp Gln Thr Leu Ala Val Tyr Gln Gln
 50                  55                  60
```

```
Val Leu Thr Ser Leu Pro Ser Gln Asn Val Leu Gln Ile Ala Asn Asp
 65              70                  75                  80

Leu Glu Asn Leu Arg Asp Leu Leu His Leu Leu Ala Phe Ser Lys Ser
             85                  90                  95

Cys Ser Leu Pro Gln Thr Ser Gly Leu Gln Lys Pro Glu Ser Leu Asp
            100             105             110

Gly Val Leu Glu Ala Ser Leu Tyr Ser Thr Glu Val Val Ala Leu Ser
        115             120             125

Arg Leu Gln Gly Ser Leu Gln Asp Ile Leu Gln Gln Val Asp Leu Ser
    130             135             140

Pro Gly Cys
145
```

COMPOSITION-OF-MATTER AND METHOD FOR TREATING CARDIOVASCULAR DISORDERS

FIELD AND BACKGROUND OF THE INVENTION

The present invention relates to a composition-of-matter and methods of using same for treating cardiovascular disorders and, more particularly, to a composition-of-matter formulated for local release of an anti-leptin at the site of treatment Cardiovascular disease (CVD) is a class of diseases that involve the heart and/or the blood vessels. Several studies have related inflammatory markers to cardiovascular disease (CVD) and several assays for inflammatory markers are commercially available. For example, C-reactive protein (CRP), a common inflammatory marker, has been found to be present in increased levels in patients who are at risk for cardiovascular disease [Karakas and Koenig, 2009 Herz 34 (8): 607-13] while osteo-protegerin, which is involved with regulation of NF-κB, has been found to be a risk factor for cardiovascular disease and mortality [Venuraju et al., 2010 J. Am. Coll. Cardiol. 55 (19): 2049-61].

As a result of these findings, the number of inflammatory marker tests ordered by clinicians for CVD risk prediction has grown rapidly. However, to date there is no consensus among professionals as to how these markers of inflammation should be used as a basis for clinical treatment.

Although it has been shown that some cardiovascular disorders can benefit from suppression of inflammation-related processes and cellular proliferation as part of a remodeling response [e.g. use of locally released cytotoxic drugs such as paclitaxel or sirolimus in preventing restenosis or use of doxycycline in treatment of abdominal aortic aneurysm (AAA)], to date, there is no evidence to suggest that cardiovascular disease can benefit from anti-inflammatory treatment.

Leptin is a pleiotropic molecule that regulates food intake as well as metabolic and endocrine functions. Leptin also plays a regulatory role in immunity, inflammation, and hematopoiesis. Although it has been proposed that leptin might play a role in vascular inflammation, oxidative stress, and vascular smooth muscle hypertrophy that may contribute to coronary heart disease among other pathologies, to date no one has conclusively shown that localized down-regulation of leptin activity can be used to treat cardiovascular disorders characterized by remodeling of cardiovascular tissue such as cardiac, arterial or valve tissue.

While reducing the present invention to practice, the present inventor has shown that down-regulation of leptin activity at specific sites in the cardiovascular system can lead to suppression and reversal of pathological tissue remodeling and thereby establishing localized leptin down-regulation as a suitable approach for treating various cardiovascular disorders characterized by pathological tissue remodeling.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2 illustrates a balloon catheter configured for local release of a leptin antagonist (drug release indicated by arrows).

DESCRIPTION OF THE PREFERRED EMBODIMENTS

Figure 1B:
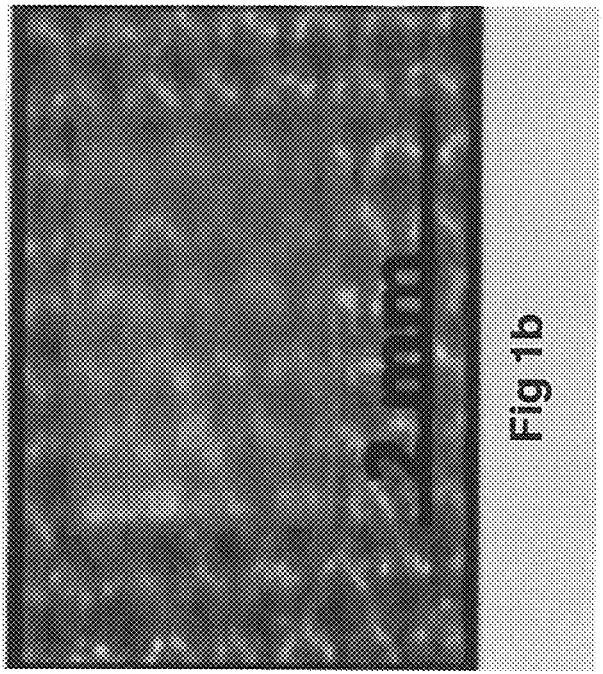
FIG. 1a-c illustrate a gel (FIG. 1a), film (FIG. 1b) and mesh (FIG. 1c) for local release of a leptin antagonist.

The present invention is of an anti-leptin composition which can be used for localized suppression of leptin-related tissue remodeling processes. Specifically, the present invention can be used to treat and attenuate expansion of ascending aortic aneurysm, and corresponding cardiac sequelae (driven by the aorto-ventricular coupling), including left ventricular hypertrophy, as well as hyperplasia of left heart valve leaflets. The present invention can also be used to treat peripheral vascular disorders such as the progression of arterial or venous aneurysms while minimizing systemic exposure to the exogenous agent delivered thereby.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present inventor set out to elucidate the role of leptin in cardiovascular disorders by employing a leptin antagonist in a localized manner. Experiments conducted by the present inventor (see Examples section hereinbelow) demonstrated that localized release of leptin in cardiovascular tissue can lead to cardiovascular tissue remodeling while localized down-regulation of leptin activity can lead to suppression and even reversal of cardiovascular tissue (arterial wall tissue, heart muscle tissue and valve leaflet tissue) remodeling induced by angiotensin II. Thus, the present inventor has shown for the first time that a locally administered leptin antagonist can be used to treat cardiovascular disorders characterized by tissue remodeling.

Thus, according to one aspect of the present invention there is provided a composition-of-matter for treating cardiovascular disorders. As used herein, "cardiovascular disorders" refer to disorders of the cardiovascular system, i.e. the heart and central, cranial and peripheral vasculature. Examples of such disorders include, but are not limited to valve stenosis, aneurysms, cardiomyopathy and the like.

The composition of the present invention includes a leptin antagonist and a carrier configured for localized release of the leptin antagonist in cardiovascular tissue.

The carrier can be a solid, gel or liquid carrier, while the leptin antagonist can be any agent capable of down-regulating leptin activity in the target tissue. Examples of a leptin antagonist include agents capable of binding and/or degrading leptin or leptin receptors as well as agents capable of down-regulating leptin expression (at the DNA or RNA levels, i.e. agents capable of blocking transcription or translation).

One example of an agent capable of down-regulating leptin is an antibody or antibody fragment capable of specifically binding leptin or a leptin receptor. Preferably, the antibody specifically binds at least one epitope of leptin, e.g. an epitope defined amino acids 26-59 of mammalian leptin (e.g. rat leptin). As used herein, the term "epitope" refers to any antigenic determinant on an antigen to which the paratope of an antibody binds.

As used herein, the term "antibody" refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

In cases where target antigens are too small to elicit an adequate immunogenic response, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in *E. coli* or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as *E. coli*. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of *Escherichia coli*. Biotechnology (N.Y.) 11(11), 1271-1277; and U.S. Pat. No. 4,946,778).

Isolated complementarity-determining region peptides can be obtained by constructing genes encoding the CDR of an antibody of interest Such genes may be prepared, for example, by RT-FCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human therapy, humanized antibodies are preferred. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunization. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633, 425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View; Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

Anti-leptin antibodies as well as epitope sequences suitable for generating antibodies and antibody fragments are described in US20070104708 which is incorporated herein by reference.

Leptin peptide antagonists can also be used with the present invention. One leptin antagonist, a modified mammalian leptin polypeptide termed superactive leptin mutein is disclosed in US20130133089 which is fully incorporated herein by reference. US20130133089 discloses high affinity mammalian leptin antagonists, in which the LDFI hydrophobic binding site at the position corresponding to positions 39-42 of the wild-type human leptin (SEQ ID NO: 2) is modified such that from two to four amino acid residues of the hydrophobic binding site are substituted with different amino acid residues such that the site becomes less hydrophobic, and the aspartic acid at the position corresponding to position 23 of the wild-type human leptin (D23) is substituted with a different amino acid residue that is not negatively charged. In specific embodiments, the high affinity leptin antagonists are D23L/L39A/D40A/F41A muteins of mammalian leptin, including the superactive human leptin antagonist (SHLA) having the amino acid sequence of SEQ ID NO: 1, and the superactive mouse leptin antagonist (SMLA) having the amino acid sequence of SEQ ID NO: 3.

The term "peptide" as used herein encompass native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

Peptide bonds (—CO—NH—) within the peptide may be substituted, for example, by N-methylated bonds (—N(CH3)-CO—); ester bonds (—C(R)H—C—O—O—C(R)—N—); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH—); olefinic double bonds (—CH=CH—); retro amide bonds (—NH—CO—); and peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr, and Phe, may be substituted for synthetic non-natural acids such as, for instance, tetrahydroisoquinoline-3-carboxylic acid (TIC), naphthylelanine (Nol), ring-methylated derivatives of Phe, halogenated derivatives of Phe, and o-methyl-Tyr.

In addition to the above, the peptides of the present invention may also include one or more modified amino acids or one or more non-amino acid monomers (e.g., fatty acids, complex carbohydrates, etc.).

The term "amino acid" or "amino acids" is understood to include the 20 naturally occurring amino acids; those amino acids often modified post-translationally in vivo, including, for example, hydroxyproline, phosphoserine, and phosphothreonine; and other less common amino acids, including but not limited to 2-aminoadipic acid, hydroxylysine, isodesmosine, nor-valine, nor-leucine, and ornithine. Furthermore, the term "amino acid" includes both D- and L-amino acids.

The peptides of the present invention are preferably utilized in a linear form, although it will be appreciated that in cases where cyclization does not severely interfere with peptide characteristics (e.g. receptor binding), cyclic forms of the peptide can also be utilized.

The peptides of the present invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth. Further description of peptide synthesis is disclosed in U.S. Pat. No. 6,472,505. A preferred method of preparing the peptide compounds of the present invention involves solid-phase peptide synthesis, utilizing a solid support.

The peptide of the present invention can also be generated using cell expression approaches by utilizing expression vectors for prokaryotic or eukaryotic expression or alternatively, the peptide can be expressed in-situ by delivering a suitable expression construct to cardiovascular tissue.

To express the peptide sequence in cardiovascular cells, a polynucleotide sequence encoding the peptide (see, for example, US20130133089) is preferably ligated into a nucleic acid construct suitable for mammalian cell expression. Such a nucleic acid construct includes a promoter sequence for directing transcription of the polynucleotide sequence in the cell in a constitutive or inducible manner.

Constitutive promoters suitable for use with the present invention are promoter sequences that are active under most environmental conditions and most types of cells, such as the cytomegalovirus (CMV) and Rous sarcoma virus (RSV).

Polyadenylation sequences can also be added to the expression vector in order to increase the efficiency of mRNA translation. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Strategene, pTRES which is available from Clontech, and their derivatives.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Barr virus include pHEBO and p2O5. Other exemplary vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (Ac-MNPV), as described by Liang, C. Y. et al. (2004). High efficiency gene transfer into mammalian kidney cells using baculovirus vectors. Arch Virol 149, 51-60.

Recombinant viral vectors are useful for in vivo expression of a leptin peptide since they offer advantages such as lateral infection and targeting specificity. Lateral infection is inherent in the life cycle of retrovirus, for example, and is the process by which a single infected cell produces many progeny virions that bud of and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Figure 1A:
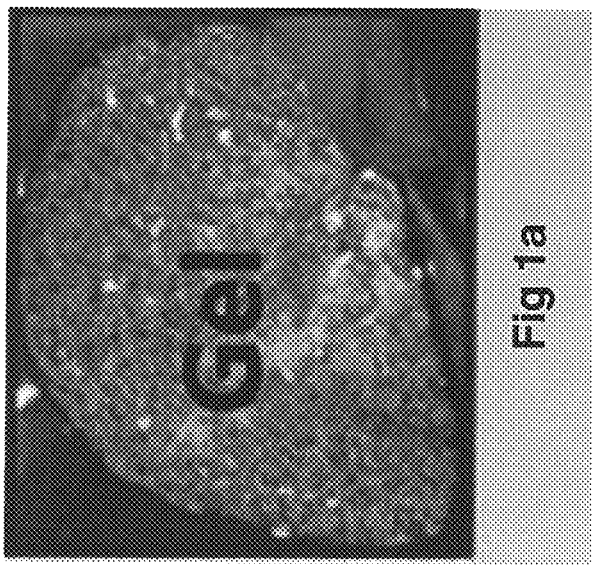
Figure 1C:
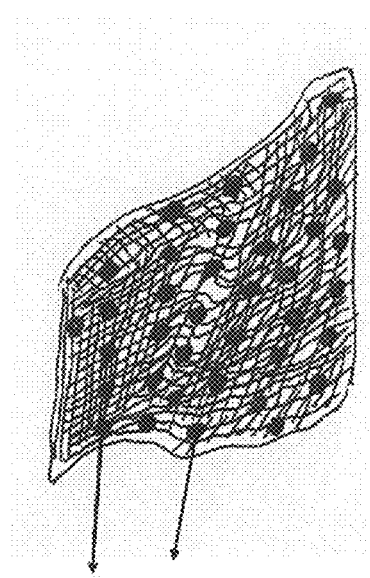
Figure 3:
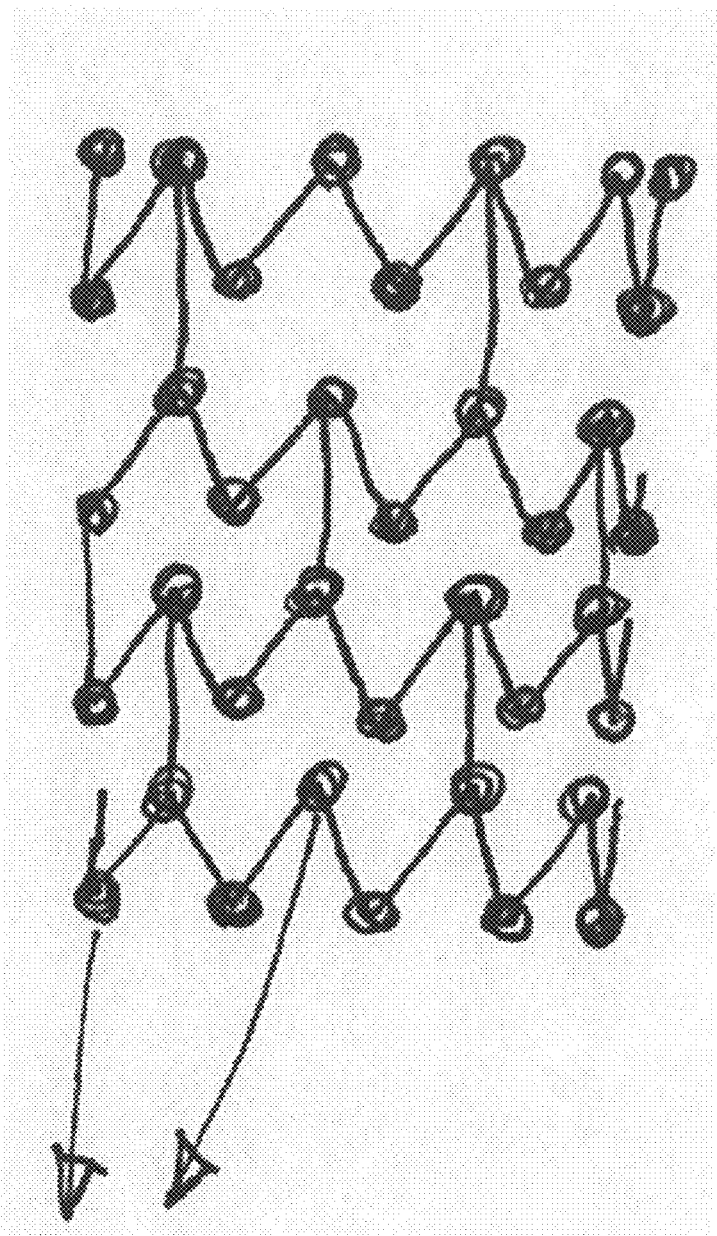
FIG. 3 illustrates a slow release leptin antagonist eluted from a scaffold.

As is mentioned hereinabove, the present composition-of-matter also includes a carrier for local delivery of the leptin antagonist. Such a carrier can be a mesh (FIG. 1c) an injectable gel (e.g. in-situ forming depot) (FIG. 1a), a thin (preferably biodegradable) film (FIG. 1b), a scaffold (FIG. 3) or a balloon catheter (FIG. 2).

Examples of in-situ formed depots include semi-solid polymers which can be injected as a melt and form a depot upon cooling to body temperature or two part systems which gel upon mixing (FIG. 3a).

The requirements for a semi-solid ISFDs include low melting or glass transition temperatures in the range of 25-65° C. and an intrinsic viscosity in the range of 0.05-0.8 dl/g [12-14]. Below the viscosity threshold of 0.05 dl/g no delayed diffusion could be observed, whereas above 0.8 dl/g the ISFD was no longer injectable using a needle. At injection temperatures above 37° C. but below 65° C. these polymers behave like viscous fluids which solidify to highly viscous depots. Drugs are incorporated into the molten polymer by mixing without the application of solvents. Thermoplastic pastes (TP) can be used to generate a subcutaneous drug reservoir from which diffusion occurs into the systemic circulation.

In situ cross-linked polymer systems utilize a cross-linked polymer network to control the diffusion of bioactive agents (e.g. leptin antagonist peptides) over a prolonged period of time. Use of in situ cross-linking implants necessitate protection of the bioactive agents during the cross-linking reaction. This could be achieved by encapsulation into fast degrading gelatin microparticles.

An ISFD can also be based on polymer precipitation. A water-insoluble and biodegradable polymer is dissolved in a biocompatible organic solvent to which a drug is added forming a solution or suspension after mixing. When this formulation is injected into the body the water miscible organic solvent dissipates and water penetrates into the organic phase. This leads to phase separation and precipitation of the polymer forming a depot at the site of injection. One example of such a system is Atrigele™ (ARM Laboratories).

Thermally induced gelling systems can also be used as ISFDs. Numerous polymers show abrupt changes in solubility as a function of environmental temperature. The prototypic thermosensitive polymer is poly(N-isopropyl acryl amide), poly-NIPAAM, which exhibits a rather sharp lower critical solution temperature.

Thermoplastic pastes such as the new generation of poly(ortho-esters) developed by AP Pharma can also be used for depot drug delivery. Such pastes include polymers that are semi-solid at room temperature, hence heating for drug incorporation and injection is no longer necessary. Injection is possible through needles no larger than 22 gauge. The drug can be mixed into the systems in a dry and, therefore, stabilized state. Shrinkage or swelling upon injection is thought to be marginal and, therefore, the initial drug burst is expected to be lower than in the other types of ISFD. An additional advantage is afforded by the self-catalyzed degradation by surface erosion.

The IFSD can be formulated for sustained-release (SR), extended-release (ER, XR, or XL), time-release or timed-release, controlled-release (CR), or continuous-release.

Examples of thin films (FIG. 3b) suitable for release of a leptin antagonist (or polynucleotide encoding same) include polymeric films [for a review of thin films, see Zelikin ACS Nano, 2010, 4 (5), pp 2494-2509; Venkat et al. 2010, Polymer Thin Films for Biomedical Applications, Wiley VCH Verlag GmbH & Co. KGaA, Wein-helm]. The thin film carrier can be biodegradable or dissolvable over time.

Biodegradable microsphere fabricated from, for example, PLA, PGA or PLGA can also be used for local delivery of a leptin antagonist. Such microspheres can be produced as described by Kim and Park (J Control Release, 2004 Jul. 23; 98(1):115-25).

A balloon such as an angioplasty balloon (FIG. 2) can also be used to deliver a leptin antagonist to a vascular wall or an inner wall of a heart chamber. Approach for coating/loading a balloon with a peptide are described in EP2643030; U.S. Pat. No. 8,617,136; U.S. Pat. No. 8,617,104; U.S. Pat. No. 8,617,114; WO1997017099; US20110166547 and US20120150142.

Although delivery of leptin or leptin receptor binding agents such as those described above (or expression thereof in cardiovascular cells), is presently preferred, downregulation of leptin activity at specific tissues can also be effected at the transcript level using a variety of molecules that interfere with transcription and/or translation (e.g., antisense, siRNA, Ribozyme, or DNAzyme).

RNA interference can be used to downregulate endogenous leptin via a small interfering RNA (siRNA) molecule. RNAi is a two-step process, in the first, the initiation step, input double-stranded (dsRNA) is digested into 21- to 23-nucleotide (nt) small interfering RNAs (siRNAs), probably by the action of Dicer, a member of the RNase III family of dsRNA-specific ribonucleases, which processes (cleaves) dsRNA (introduced directly or by means of a transgene or a virus) in an ATP-dependent manner. Successive cleavage events degrade the RNA to 19- to 21-bp duplexes (the siRNA), each with 2-nucleotide 3' overhangs (Hutvagner, G. and Zamore. P. D. (2002). RNAi: Nature abhors a double-strand. Curr Opin Gen Dev 12, 225-232; and Bernstein, E. (2001). Role for a bidentate ribonuclease in the initiation step of RNA interference. Nature 409, 363-366).

In the second step, termed the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base-pairing interactions and cleaves the mRNA into 12-nucleotide fragments from the 3' terminus of the siRNA (Hutvagner and Zamore (2002); Hammond et al. (2001) Nat. Rev. Gen. 2:110-119 (2001); and Sharp, P. A. (2001). RNA interference. Genes Dev 15, 485-490). Although the mechanism of cleavage remains to be elucidated, research indicates that each RISC contains a single siRNA and an RNase (Hutvagner and Zamore (2002)).

Synthesis of RNAi molecules suitable for use with the present invention can be effected as follows. First, the leptin mRNA sequence is scanned downstream of the AUG start codon for AA-dinucleotide sequences. Occurrence of each AA and the 19 3'-adjacent nucleotides is recorded as a potential siRNA target site. Preferably, siRNA target sites are selected from the open reading frame (ORF), as untranslated regions (UTRs) are richer in regulatory protein binding sites. UTR-binding proteins and/or translation initiation complexes may interfere with binding of the siRNA endonuclease complex (Tuschl (2001)). It will be appreciated, however, that siRNAs directed at untranslated regions may also be effective, as demonstrated for GAPDH, wherein siRNA directed at the 5' UTR mediated about a 90% decrease in cellular GAPDH mRNA and completely abolished protein levels (wwwdotambiondot-com/techlib/tn/91/912dothtml).

Second, potential target sites are compared to an appropriate genomic database (e.g., human, mouse, rat, etc.) using any sequence alignment software, such as the BlastN software available from the NCBI server (wwwdotncbidotnlm-dotnihdotgov/BLAST/). Putative target sites that exhibit significant homology to other coding sequences are filtered out.

Qualifying target sequences are selected as templates for siRNA synthesis. Preferred sequences are those including low G/C content, as these have proven to be more effective in mediating gene silencing as compared with sequences including G/C content higher than 55%. Several target sites are preferably selected along the length of the target gene for evaluation. For better evaluation of the selected siRNAs, a negative control is preferably used in conjunction. Negative-control siRNAs preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating leptin is a DNAzyme molecule, which is capable of specifically cleaving an mRNA transcript or a DNA sequence of the leptin. DNAzymes are single-stranded polynucleotides that are capable of cleaving both single- and double-stranded target sequences (Breaker, R. R. and Joyce, G. F. (1995). A DNA enzyme with $Mg^{2+}$-dependent RNA phosphoesterase activity. Curr Biol 2, 655-660; Santoro, S. W. and Joyce, G. F. (1997). A general purpose RNA-cleaving DNA enzyme. Proc Natl Acad Sci USA 94, 4262-4266). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro and Joyce (1997)); for review of DNAzymes, see: Khachigian, L. M. (2002). DNAzymes: cutting a path to a new class of therapeutics. Curr Opin Mol Ther 4, 119-121.

Examples of construction and amplification of synthetic, engineered DNAzymes recognizing single- and double-stranded target cleavage sites are disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh, T. et al., Abstract 409, American Society of Gene Therapy 5th Annual Meeting (wwwdotasgtdotorg), Jun. 5-9, 2002, Boston, Mass. USA.). In another application, DNAzymes complementary to bcr-abl oncogenes were successful in inhibiting the oncogene's expression in leukemia cells, and in reducing relapse rates in autologous bone marrow transplants in cases of Chronic Myelogenous Leukemia (CML) and Acute Lymphoblastic Leukemia (ALL).

Downregulation of leptin can also be effected by using an antisense polynucleotide capable of specifically hybridizing with an mRNA transcript encoding leptin.

Design of antisense molecules that can be used to efficiently downregulate a leptin must be effected while considering two aspects important to the antisense approach. The first aspect is delivery of the oligonucleotide into the cytoplasm of the appropriate cells, while the second aspect is design of an oligonucleotide that specifically binds the designated mRNA within cells in a manner inhibiting the translation thereof.

The prior art teaches of a number of delivery strategies which can be used to efficiently deliver oligonucleotides into a wide variety of cell types (see, for example: Luft, F. C. (1998). Making sense out of antisense oligodeoxynucleotide delivery: getting there is half the fun. J Mol Med 76(2), 75-76 (1998); Kronenwett et al. (1998). Oligodeoxyribonucleotide uptake in primary human hematopoietic cells is enhanced by cationic lipids and depends on the hematopoietic cell subset. Blood 91, 852-862; Rajur, S. B. et al. (1997). Covalent protein-oligonucleotide conjugates for efficient delivery of antisense molecules. Bioconjug Chem 8, 935-940; Lavigne et al. Biochem Biophys Res Commun 237: 566-71 (1997); and Aoki, M. et al. (1997). In vivo transfer efficiency of antisense oligonucleotides into the myocardium using HVJ-liposome method. Biochem Biophys Res Commun 231, 540-545).

In addition, also available are algorithms for identifying those sequences with the highest predicted binding affinity for their target mRNA based on a thermodynamic cycle that accounts for the energetics of structural alterations in both the target mRNA and the oligonucleotide (see, for example, Walton, S. P. et al. (1999). Prediction of antisense oligonucleotide binding affinity to a structured RNA target. Biotechnol Bioeng 65, 1-9).

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF-alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiencies of specific oligonucleotides using an in vitro system were also published (Matveeva, O. et al. (1998). Prediction of antisense oligonucleotide efficacy by in vitro methods. Nature Biotechnology 16, 1374-1375).

Another agent capable of down-regulating leptin is a ribozyme molecule capable of specifically cleaving an mRNA transcript encoding leptin. Ribozymes increasingly are being used for the sequence-specific inhibition of gene expression by the cleavage of mRNAs encoding proteins of interest (Welch, P. J. et al. (1998). Expression of ribozymes in gene transfer systems to modulate target RNA levels. Curr Opin Biotechnol 9, 486-496).

An additional method of regulating the expression of leptin in cardiovascular cells is via triplex-forming oligonucleotides (TFOs). Recent studies show that TFOs can be designed to recognize and bind to polypurine or polypirimidine regions in double-stranded helical DNA in a sequence-specific manner. These recognition rules are outlined in: Maher III, L. J., et al. (1989). Inhibition of DNA binding proteins by oligonucleotide-directed triple helix formation. Science 245, 725-730; Moser, H. E., et al. (1987). Sequence-specific cleavage of double helical DNA by triple helix formation. Science 238, 645-650; Beal, P. A. and Dervan, P.

B. (1991). Second structural motif for recognition of DNA by oligonucleotide-directed triple-helix formation. Science 251, 1360-1363; Cooney, M., et al. (1988). Science 241, 456-459; and Hogan, M. E., et at, EP Publication 375408. Modifications of the oligonucleotides, such as the introduction of intercalators and backbone substitutions, and optimization of binding conditions (e.g., pH and cation concentration) have aided in overcoming inherent obstacles to TFO activity such as charge repulsion and instability, and it was recently shown that synthetic oligonucleotides can be targeted to specific sequences (for a recent review, see Seidman, M. M. and Glazer, P. M. (2003). The potential for gene repair via triple helix formation J Clin Invest 112, 487-494).

As is described hereinabove, the present invention can be used to treat cardiovascular disorders affecting heart or vascular tissue. The following describes several option for local delivery of a leptin antagonist to heart tissue, specifically muscle and valve tissue.

(i) Arterial catheterization can be used to apply a mesh, a thin film, or a biodegradable scaffold loaded with a leptin antagonist against a luminal wall of an ascending aorta distal to the orifice of the coronary arteries. In case of aneurysm at another location along the aorta, a visceral artery, or small tributary; the same intra-arterial approach can be used for local application.

(ii) An IFSD (gel) loaded with the leptin antagonist can be delivered via a balloon or needle to the aortic wall.

(iii) A pliable non-degradable or biodegradable mesh or film loaded with the leptin antagonist can be surgically delivered to the peri-aortic region (above the aortic root level) via open surgery, or thoracoscopy. In case of small aneurysm in the abdominal aorta the leptin antagonist slow release film or mesh can be applied via open surgery or minimally invasive laparoscopy It should be noted that application of a leptin antagonist at the ascending aorta may be effective in attenuating ascending aortic aneurysms, as well as moderating left ventricular hypertrophy, and left heart valve thickness (aortic and mitral). Application of leptin antagonist at arterial aneurysms in other locations is anticipated to achieve a similar outcome, attenuating aneurysm expansion.

Thus, the present invention can be used to treat cardiovascular disorders such as heart valve stenosis, arterial or venous aneurysms, or left ventricular remodeling by enabling localized release of a leptin antagonist at the site of treatment.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Localized Leptin Synthesis in a Mouse Model

A novel mouse model was used to simulate local leptin synthesis in the ascending aorta in order to assess the effect of leptin on aortic remodeling and heart structure and function.

Materials and Methods

Figure 4:
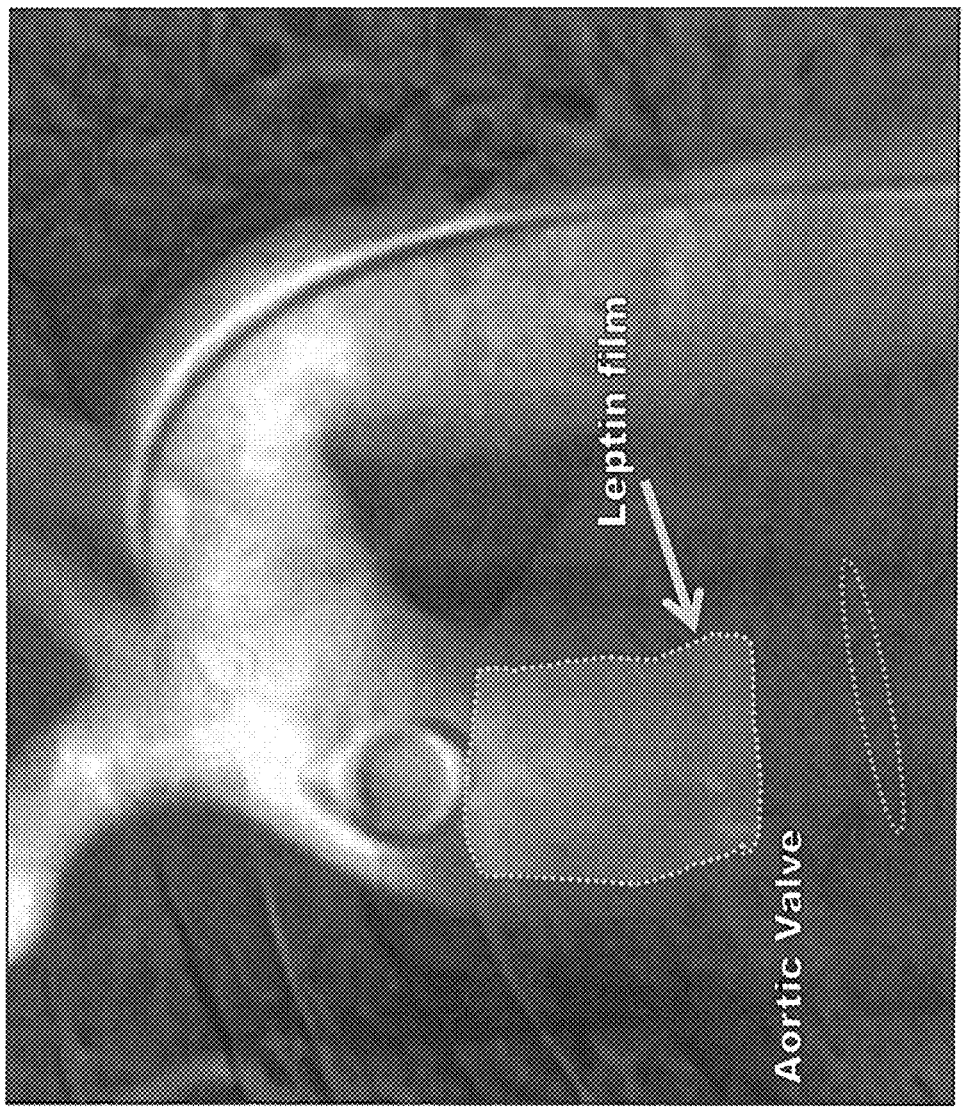
FIG. 4 illustrates the location of leptin film application on the anterior outer surface of the ascending aorta. Human arch angiogram depicts mouse anatomy.
Figure 5:
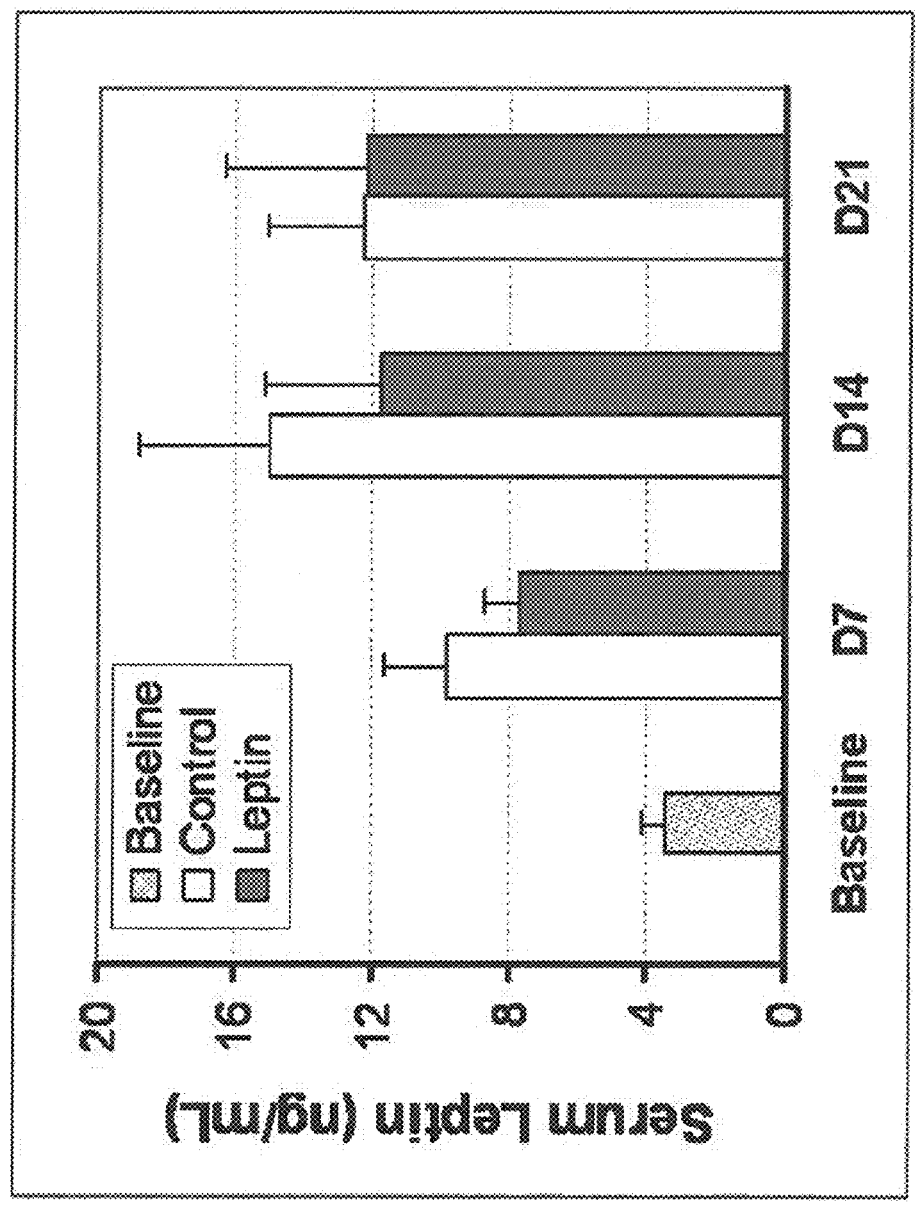
FIG. 5 illustrates a time course analysis of serum leptin level in ApoE$^{-/-}$ mice that underwent peri-aortic application of leptin film (20 μg).

A slow release leptin film (FIG. 1b) made of polylactic co-glycolic acid (PLGA) matrix (1×1.5 mm), and containing either 2 µg leptin or no protein (control) was applied to the anterior surface of the proximal ascending aorta (FIG. 4).

The leptin slow-release film was manufactured by impregnating a poly lactic-co-glycolic acid (PLGA) film with leptin. One gram of PLGA 6535 polymer (D,L-lactide: glycolide::65:35, Mw=45,000-75,000 Da; Lakeshore. Biomaterials, Birmingham, Ala., USA) was dissolved in 10 mL $MgCl_2$ (Fisher Scientific, Loughborough, UK). Sodium chloride (10 mg in 0.2 mL distilled water) and 25 µL ethylene glycol (Sigma-Aldrich, St. Louis, Mo., USA) were added to the polymeric solution and sonicated for 20 seconds. Mouse leptin powder (1 mg; #L3772; Sigma-Aldrich, St. Louis, Mo., USA) was suspended in 2 mL of the polymeric solution, followed by casting on a flat surface of Teflon molds to create a flat film. Films were dried in a hood for 48 hours, and then subjected to high vacuum for 12 hours to extract any residual solvent. Control (placebo) films were fabricated in the same way without the addition of leptin. The calculated amount of leptin per 1×1.5-mm film used currently for implantation in each mouse was 2 µg.

Another option of leptin application for local slow-release has been a gel composed of two liquid materials which gel (solidify) upon mixing at the time of injection. These are a modified carboxymethyl cellulose with adipic dihydrazide (CMC-ADH) and an oxidized dextrane in DDW (DX-COH). Methylene blue dye (0.5%) was also added to the DX-COH solution to make the resulting gel more visible. Leptin (Sigma, L3772, St. Louis, Mo., USA) was added to the gel by an emulsion technique.

Figure 6:
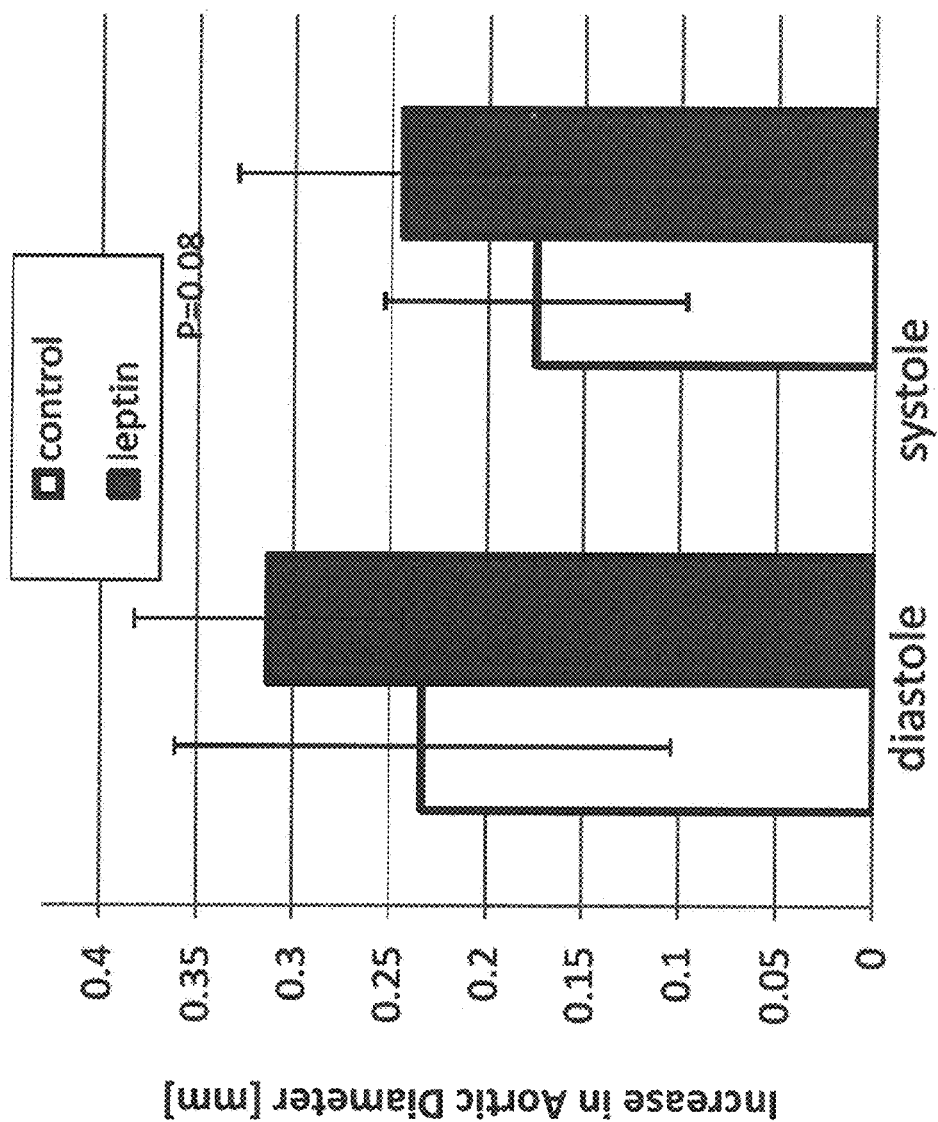
FIG. 6 illustrates increased ascending aortic diameter at the location of leptin film application versus controls.

Serum leptin levels were determined in ApoE$^{-/-}$ mice after receiving 20 µg mouse leptin via peri-aortic application (in another experiment, Tao et al. ATVB 2013). Blood was samples on days 0, 7, 14, and 21, and leptinanalyzeded by ELISA assay (Quantikine Mouse Lep Kit, R&D Systems, Minneapolis, Minn., USA): Day 0—3.5 ng/mL; day 7—leptin 8.0 ng/mL, placebo 9.2 ng/mL; day 14—leptin 12.0 ng/mL, placebo 14.5 ng/mL; and day 21—leptin 12.25 ng/mL, placebo 12.5 ng/mL (FIG. 6). Notably, these values fell within the normal range of plasma leptin in ApoE−/− mice receiving Western diet (mean 5.1±1.4 to 17±3.4 ng/mL). It should also be emphasized that circulating leptin levels are known to increase with age, as also observed in our series.

This unique mouse model was utilized to perform two experiments: Mice in experiment 1 were fed postoperatively with high fat diet (RFD), and were followed up for 45 days. In experiment 2 mice received normal chow for 30 or 60 days. Mouse weight and blood pressure (BP) were assessed weekly. All mice recovered from surgery uneventfully.

Results

In both mouse model experiments, leptin or control treated mice gained weight equally during the follow up period, suggesting no systemic leptin effect. Systolic BP measured weekly in mice of experiment 2 was 100 mmHg throughout the first 4 weeks, and increased to 120 mmHg by week 6 in both leptin treated and control mice. Based on two separate experiments, both HFD and normal chow feeding yielded in general similar results.

The following data report the results of experiment 2 (normal chow feeding).

Figure 7:
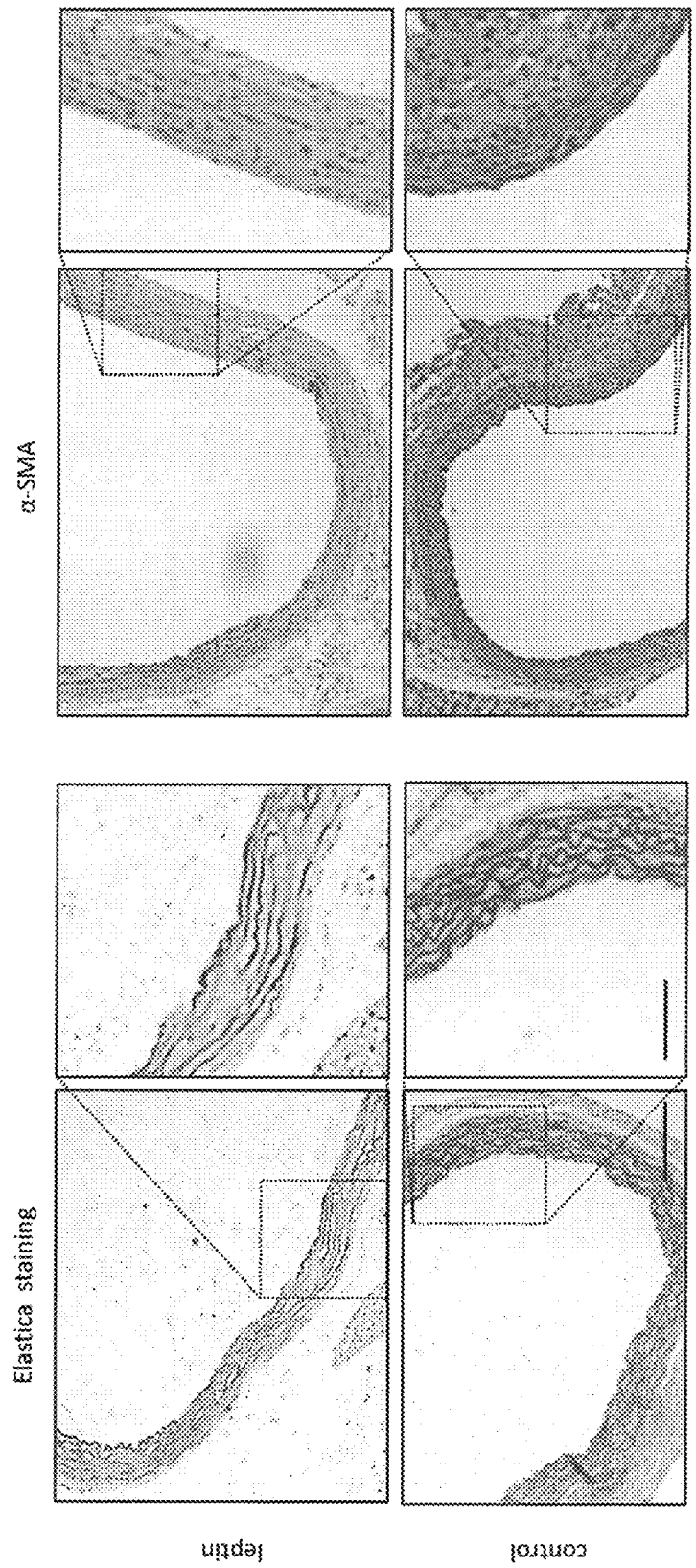
FIG. 7 illustrates elastica staining and αSMA IHC analysis of ascending aortic cross sections of mice locally treated with leptin versus controls.

Echocardiography of the ascending aorta at 2 mm distal to the aortic valve level revealed an increase in aortic diameter at peak systole in leptin treated mice vs controls (p=0.08, FIG. 6; Exp. 1 using HFD yielded P<0.003). That same aortic location exhibited decreased elasticity, which was defined as the percent increase in aortic diameter in systole vs. diastole, in leptin compared to control treated mice. There was no significant difference in diameter further distally on the ascending aorta. Notably, the aortic valve annulus did not dilate in response to local leptin application. Histological analysis of the ascending aorta revealed features of medial degeneration at the site of leptin application, including fragmentation of the elastic lamellas, as demonstrated by elastica van Giesen staining, and depletion of αSMA in the media (FIG. 7). These structural changes likely underlie local stiffening and dilatation in the proximal ascending aorta.

Figure 8:
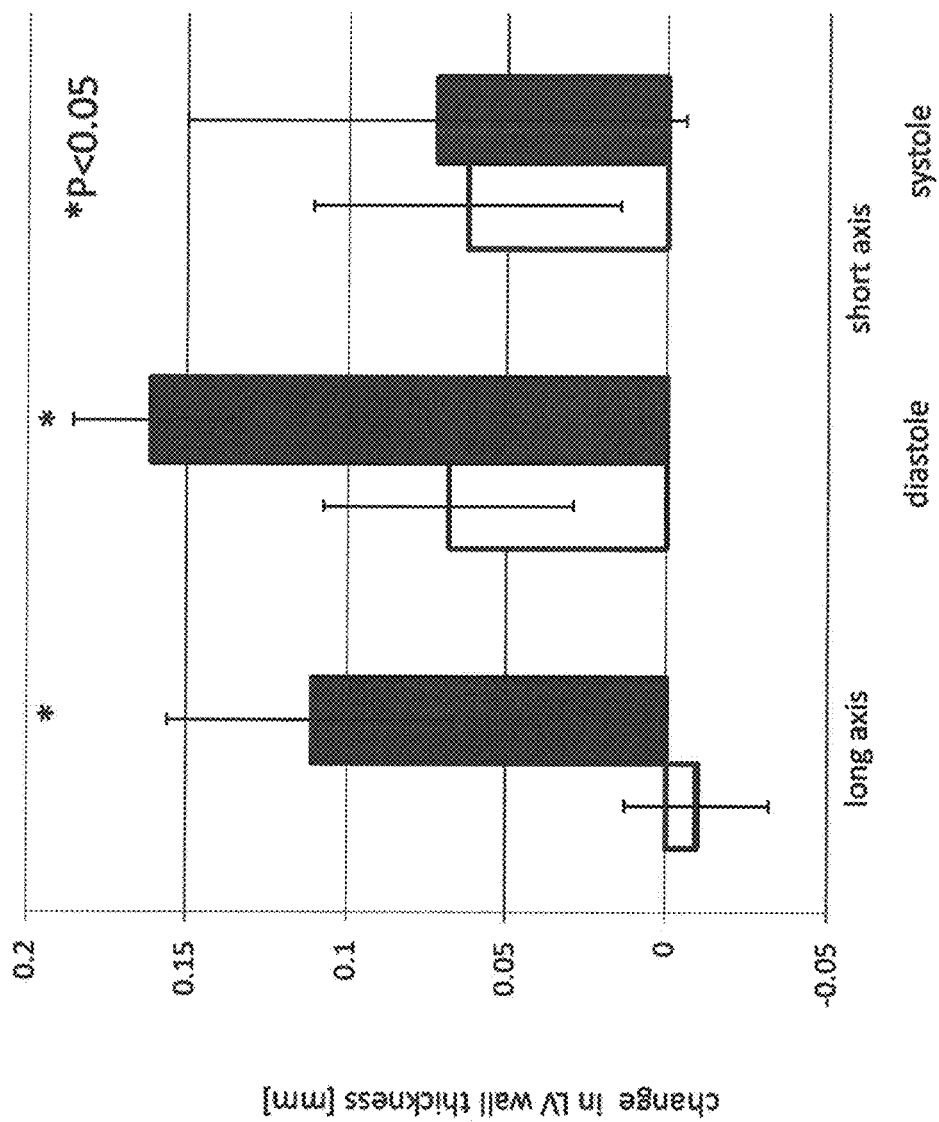
FIG. 8 illustrates change in left ventricle (LV) wall thickness in leptin-treated (filled columns) versus control (open columns) mice.
Figure 9:
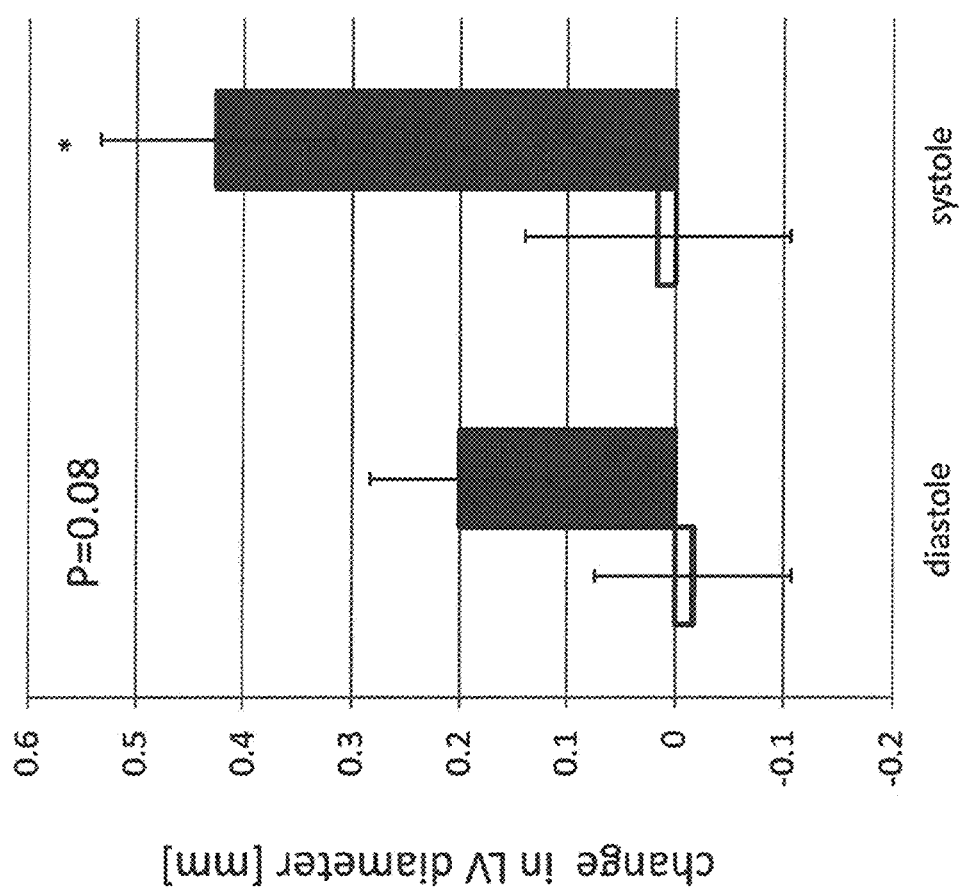
FIG. 9 illustrates LV diameter in systole and diastole in leptin-treated (filled columns) and control (open columns) mice.
Figure 10:
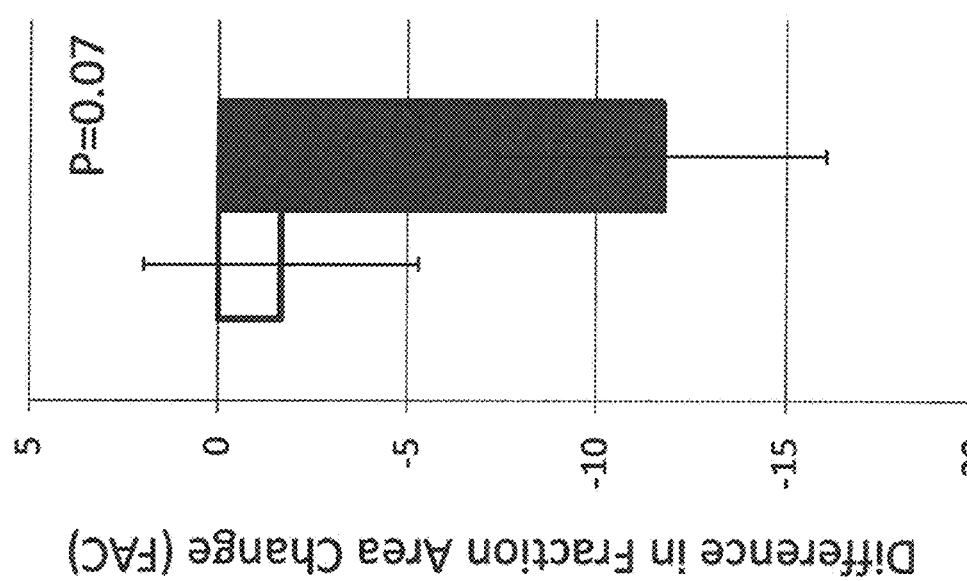
FIG. 10 illustrates LV fractional area change in leptin-treated (filled columns) versus control (open columns) mice.

Echocardiography (final vs. preoperative) revealed a concentric remodeling of the left ventricle, with hypertrophy of all LV walls (p<0.001). Wall thickening was most pronounced in diastole (p=0.002, FIG. 8). Left ventricular diameter was increased in both systole and diastole (p=0.08, p=0.02, respectively, FIG. 9), leading to a reduction in the LV fractional area change (FAC, p=0.07, FIG. 10).

Figure 11:
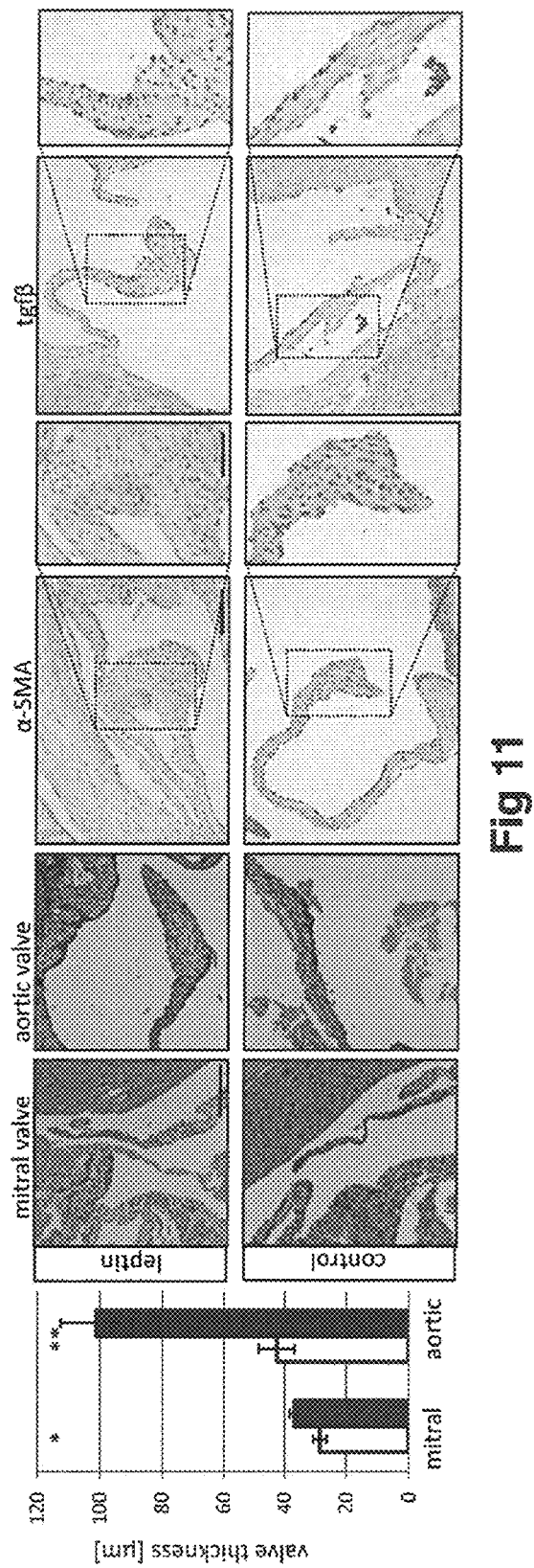
FIG. 11 illustrates aortic and mitral valve leaflet thickness in leptin-treated and control mice.

Local leptin application at the proximal ascending aorta promoted thickening of the mitral and aortic valve leaflets (p=0.01, p<0.001 accordingly, FIG. 11). Mitral leaflets were diffusely thickened, while aortic valve leaflets displayed thickening in their free edge, composed mostly of ECM and stromal cells. These proliferating cells are assumed analogous to human valvular interstitial cells (VICs). A few stromal cells within these lesions were positive for αSMA and TGFβ as shown by IHC staining (in analyzed aortic valve leaflets), suggesting VICs activation (FIG. 11). A trend was observed for increased VIC proliferation through Ki67 IHC in leptin treated mice. However, the lack of statistical significance implies that most leaflet hyperplasia took place at an earlier time.

Increased peak systolic velocity (PSV), as measured at the aortic valve in leptin treated vs control mice was short of statistical significance. However, PSV was significantly augmented in postoperative HFD fed animals.

These experiments reveal that available leptin in the proximal ascending aorta induces local aortic stiffening and dilatation. The resulting changes in local hemodynamics likely drive remodeling of the left ventricle, including LV wall hypertrophy and valve thickening through the aorto-ventricular coupling axis.

Example 2

Local Leptin Antagonism in an Ang II Mouse Model

Angiotensin II (AngII) is the key hormone of the renin-angiotensin system, underlying hypertension and cardiovascular remodeling (Renna et al. Pathophysiology of vascular remodeling in hypertension. Int J Hypertens. 2013; 2013: 808353). The phenotypes induced by local leptin application described in Example 1 are reminiscent of AngII induced aortic-ventricular (coupling) remodeling, suggesting that leptin mediates these processes. As such, a leptin antagonist was delivered locally to the ascending aorta in order to assess the effects of leptin down-regulation on AngII induced local aortic remodeling, and aortic-ventricular remodeling in mice.

Materials and Methods

Figure 12:
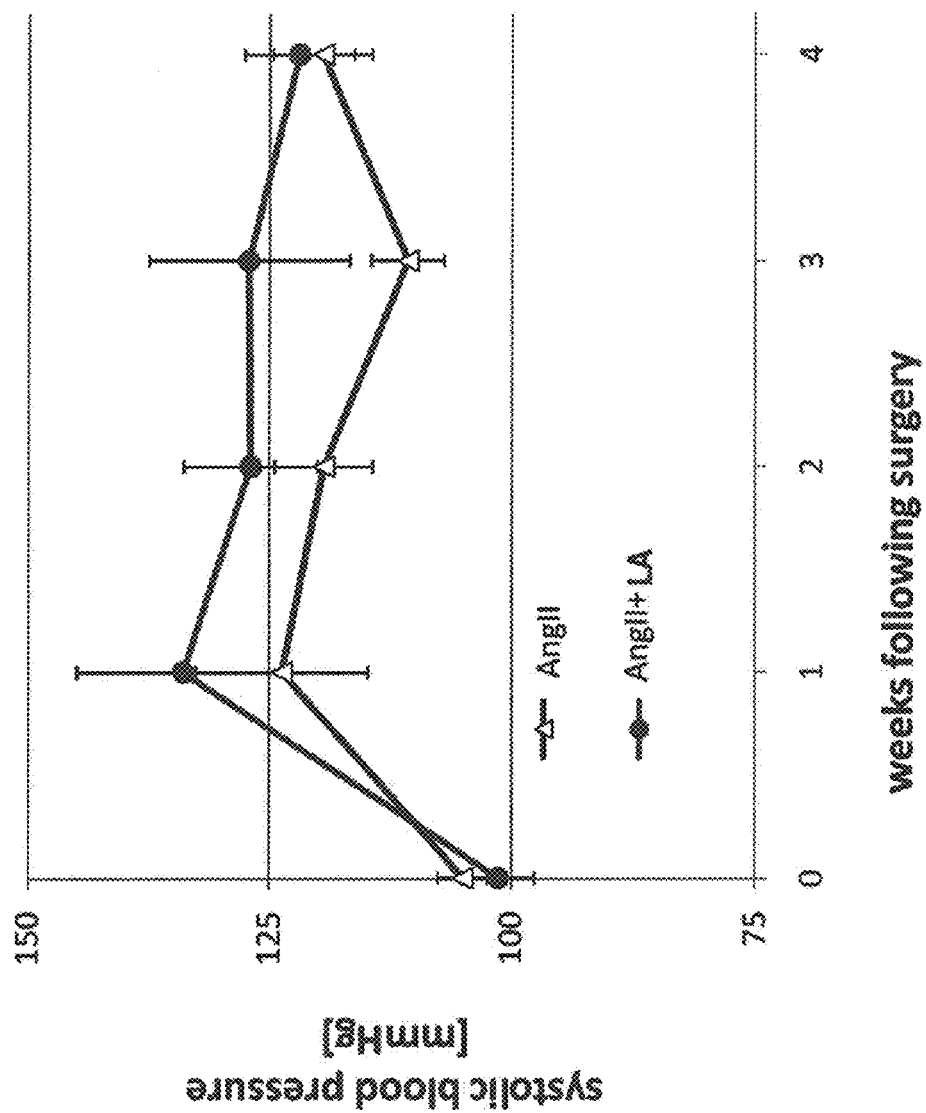
FIG. 12 illustrates mean systolic blood pressure in angiotensin II treated mice.
Figure 13:
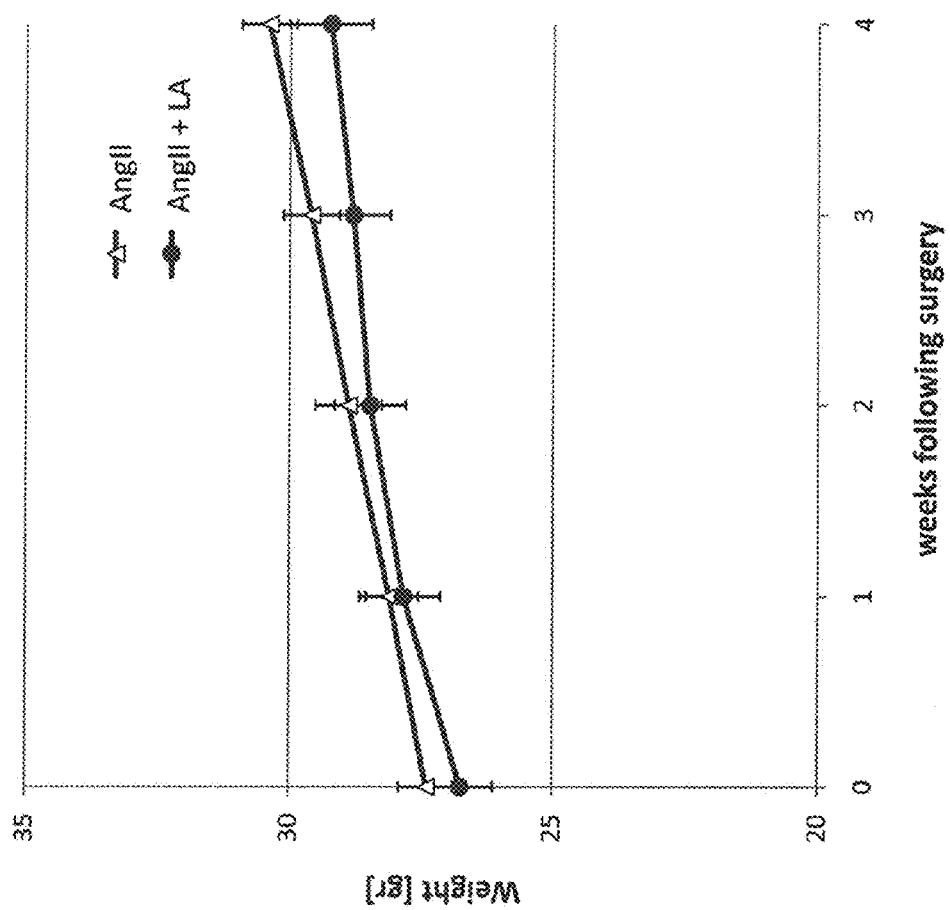
FIG. 13 illustrates a time course analysis presenting weight of angiotensin II treated mice (open triangles), and mice receiving both, angiotensin II and leptin antagonist (LA).

An osmotic mini-pump, delivering AngII at a rate of 1000 ng/kg/min was implanted subcutaneously in the back of the neck of 14 week old ApoE$^{-/-}$ mice. Each mouse also underwent left mini-thoracotomy for application of a slow release miniature PLGA film (1×1.5 mm) containing either 5 μg leptin antagonist (superactive mouse leptin antagonist, D23L/L39A/D40A/F41A leptin mutein), or PLGA matrix devoid of protein (control). The slow release film was deployed on the surface of the proximal ascending aorta at the position described in Experiment 1. Mice were euthanized 4 weeks following surgery. As expected, blood pressure assessed in both Ang II treated groups after one week was increased by approximately 20% (125 mmHg mean systolic), and was sustained throughout the follow up (FIG. 12). Weight gain pattern was similar in both groups, indicating no systemic effects related to the leptin antagonist (FIG. 13).

Results

Figure 14:
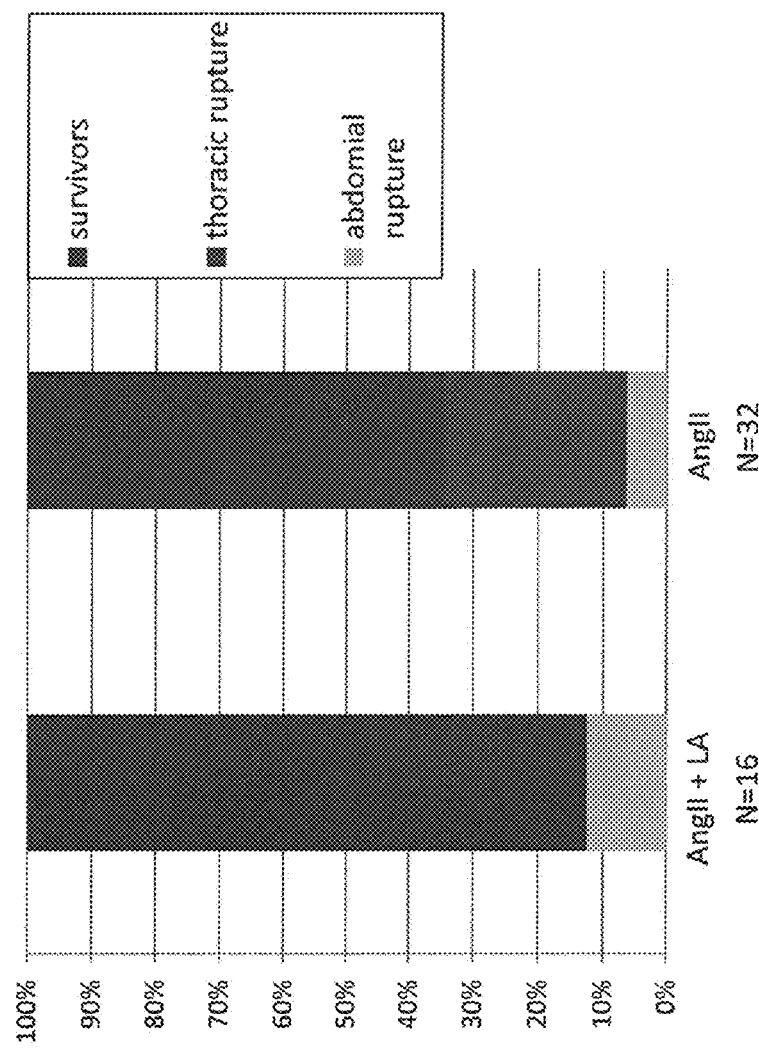
FIG. 14 illustrates number of mice that succumbed due to ruptured abdominal and thoracic aneurysms in angiotensin II treated mice versus mice receiving angiotensin II and leptin antagonist (LA).

To assess the impact of AngII alone versus AngII plus leptin antagonist on mouse longevity, mortality data from the present experiment were combined with data from a previous experiment, which included a similar cohort of ApoE$^{-/-}$ mice exposed to AngII, in same dose and duration (Tao M, et al. ATVB 2013). Collectively, a 34% mortality (referred to premature death, prior to the completion of the experiment) was observed in mice treated with AngII (either Ang II alone or Ang II with control film applied on the ascending aorta). Death was related to thoracic (28%) or abdominal (6%) aortic aneurysm rupture. Notably, mice treated with AngII that received also LA were protected from thoracic aneurysm rupture (p=0.04, FIG. 14). Death rate in mice receiving LA was only 13%, related exclusively to rupture of abdominal aortic aneurysms.

Figure 15:
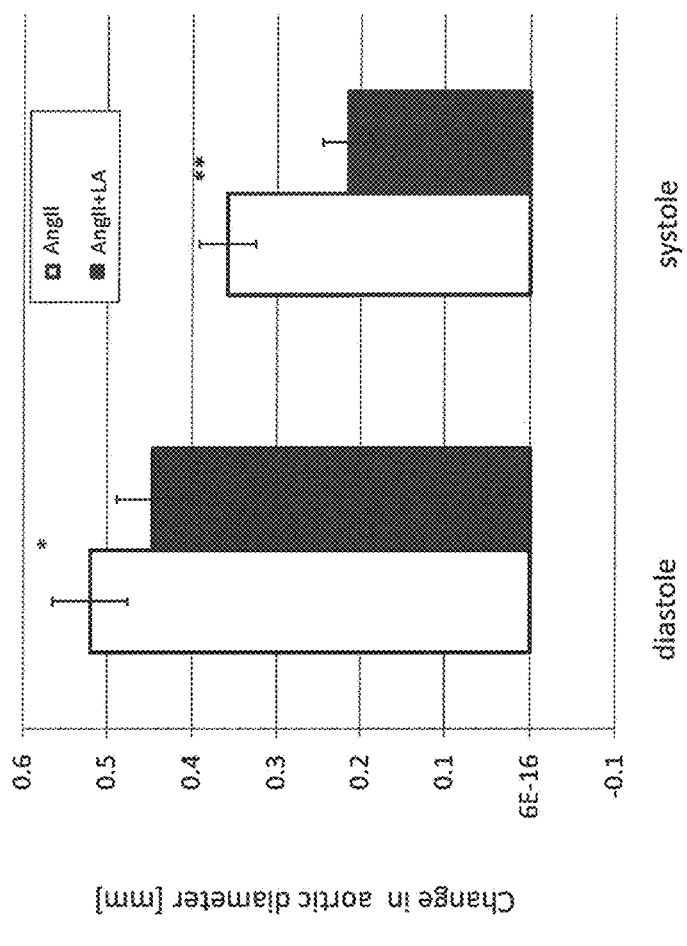
FIG. 15 illustrates ascending aortic dilatation in angiotensin II treated mice versus mice receiving angiotensin II and leptin antagonist (LA).

Echocardiograpic imaging of the ascending aorta demonstrated that local LA application in AngII treated mice significantly attenuated dilatation of the ascending aorta compared to AngII alone when measured 2 mm from the valve, at both diastole and systole (p=0.03, p=0.005, respectively, FIG. 15). However, these data did not suggest moderation of increased aortic stiffness by LA application.

Figure 16:
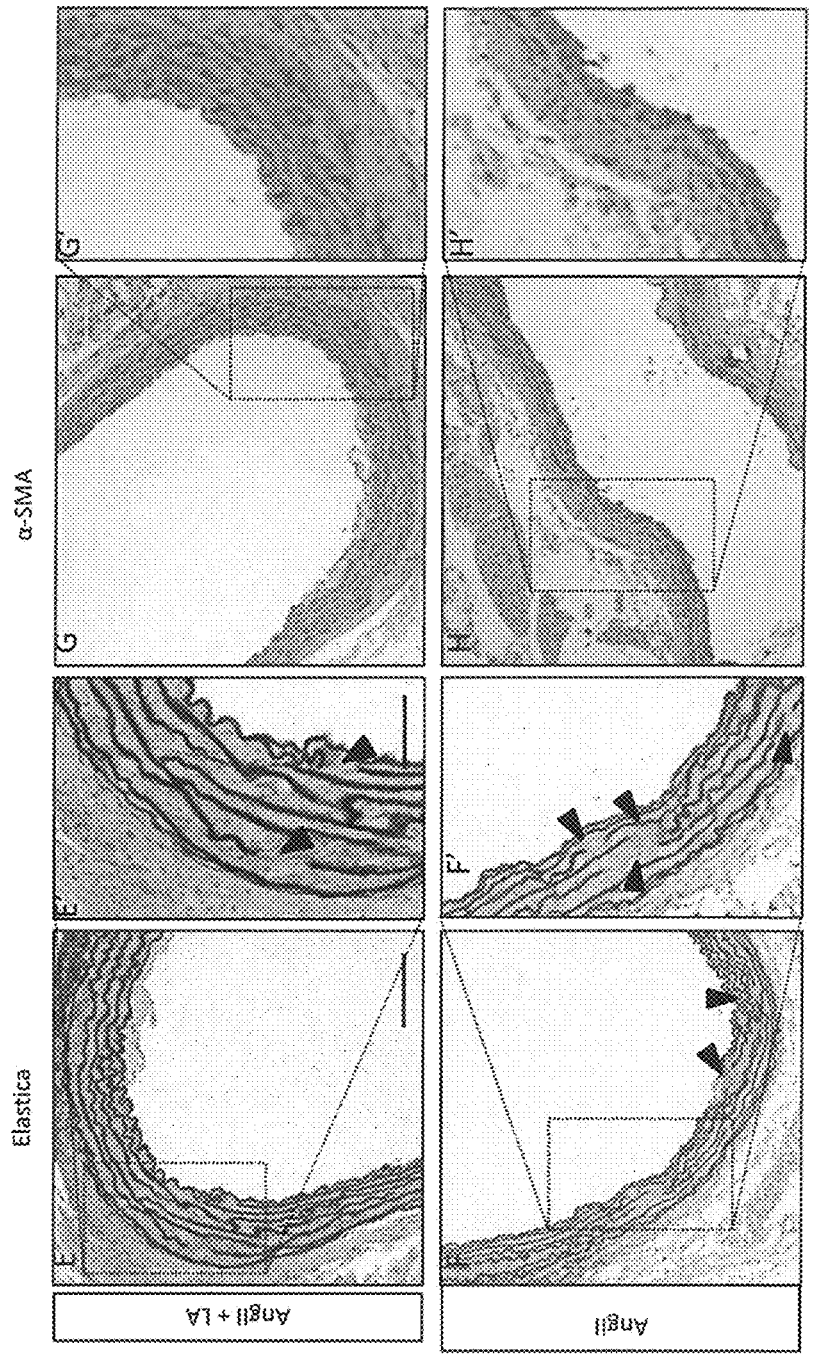
FIG. 16 illustrates elastic lamella fragmentation and αSMA depletion in angiotensin II treated mice versus mice receiving angiotensin II and leptin antagonist (LA).

Histological analysis revealed medial degeneration in both groups that were treated with AngII. Nevertheless, additional LA application resulted in less fragmentation of the elastic lamellas and fewer sites of αSMA depletion in the aortic media (FIG. 16). Notably, amongst mice receiving AngII, medial degeneration was rather diffused throughout the aorta. This was in sharp contrast to the effects of local leptin application, which exhibited medial degeneration within the segment in contact with the leptin film alone.

Figure 17:
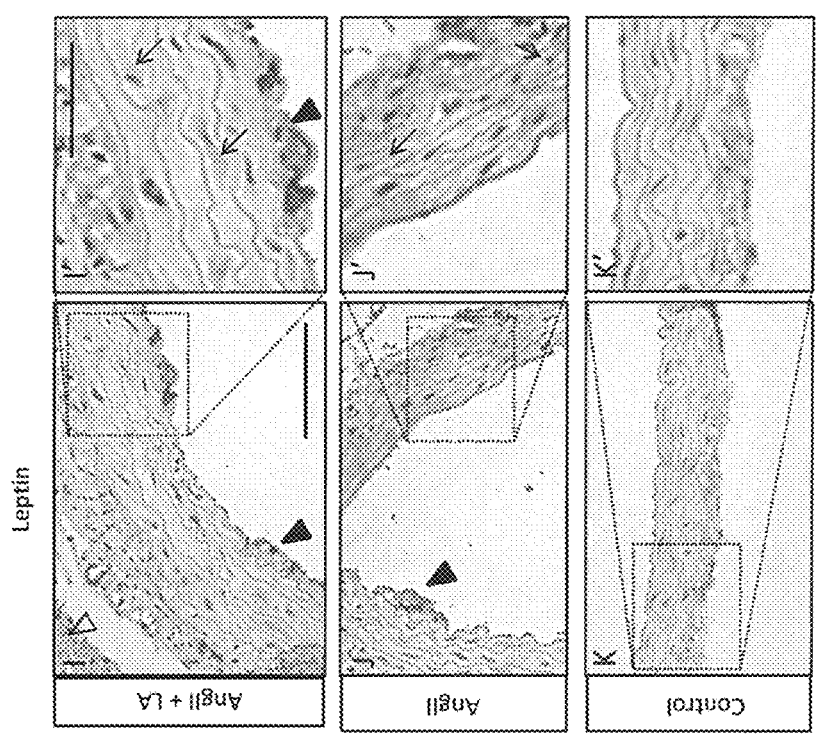
FIG. 17 illustrates leptin expression in medial SMCs (arrows) and macrophages of atherosclerotic lesions (filled arrowheads) in angiotensin II treated, angiotensin II and leptin antagonist (LA) treated, and control mice.

Immunohistochemical analysis for leptin antigen revealed a weak expression in medial SMCs, and a strong signal within foam cells of aortic luminal atherosclerotic plaques (FIG. 17).

Figure 18:
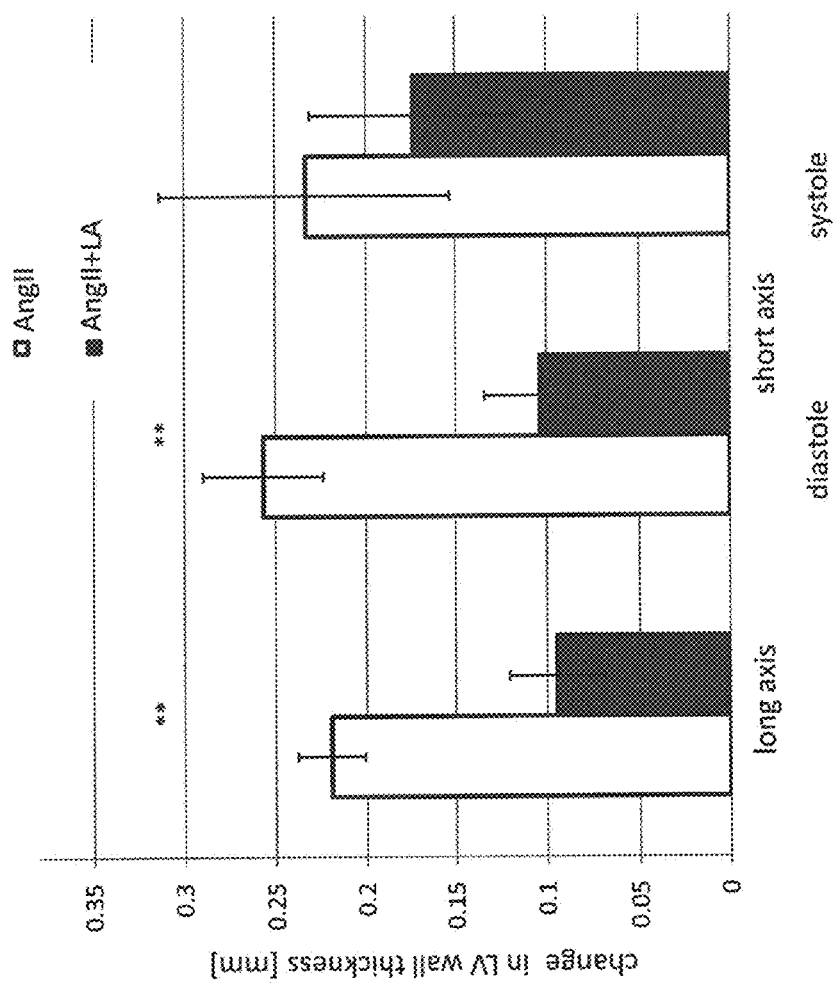
FIG. 18 illustrates LV hypertrophy in angiotensin II treated mice versus mice receiving angiotensin II and leptin antagonist (LA).
Figure 19:
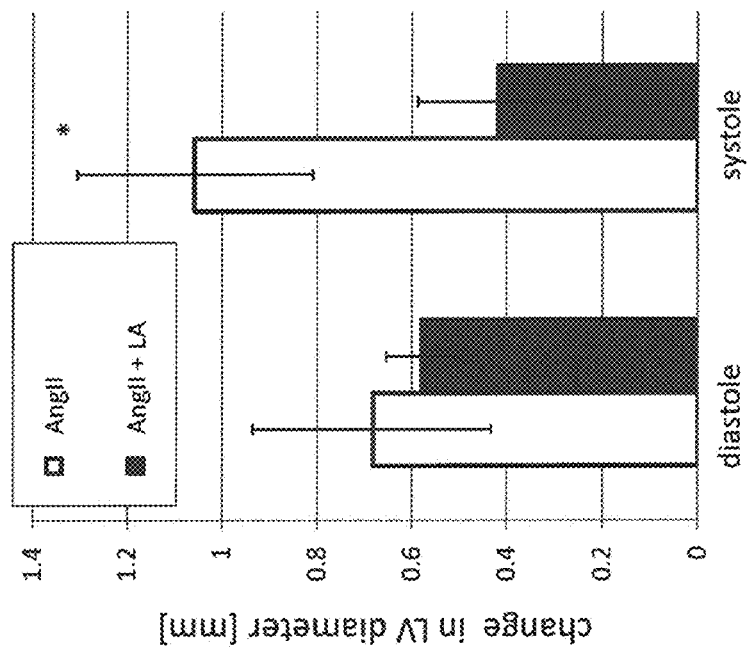
FIG. 19 illustrates changes in LV diameter in angiotensin 11 treated mice versus mice receiving angiotensin II and leptin antagonist (LA).
Figure 20:
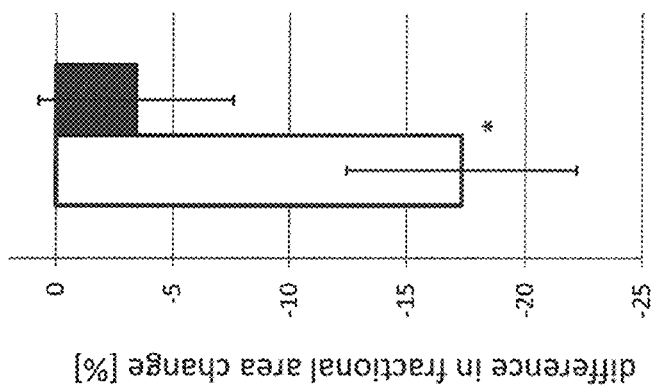
FIG. 20 illustrates LV fractional area change in angiotensin II treated mice (open column) versus mice receiving angiotensin II and leptin antagonist (LA) (filled column).

Mice treated with LA presented less thickening of the left ventricular wall, particularly in diastole (p<0.01, FIG. 18). Left ventricular diameter increased similarly in both groups in diastole however, LA treatment attenuated the increase in LV diameter during systole (p=0.05, FIG. 19). As anticipated, and corresponding to these results, a decrease in FAC in mice co-treated with AngII and LA, was observed, while mice treated by AngII alone exhibited a decrease in fractional area change by over 15% (p=0.03, FIG. 20). Moreover, LV diameter which increased in response to AngII treatment, was preserved within the baseline (pre-AngII treatment) range in the LA treated mice (P<0.05).

Figure 21:
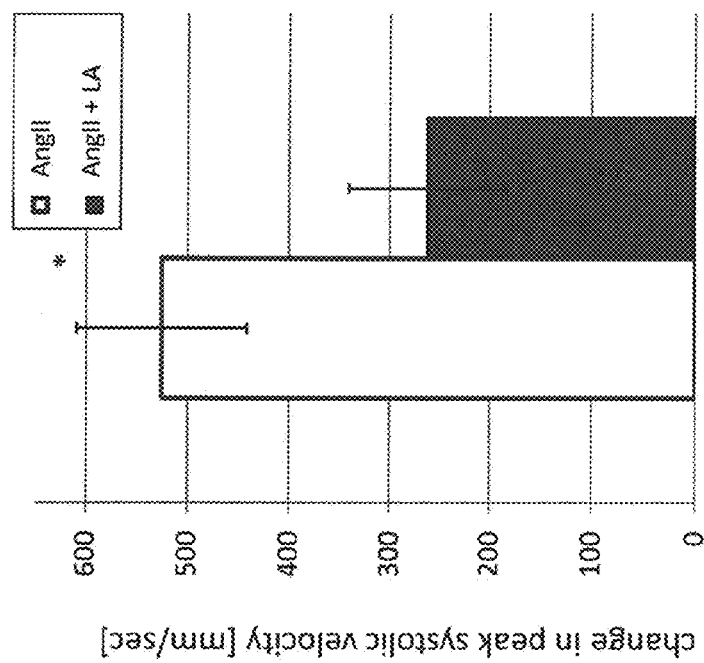
FIG. 21 illustrates peak systolic velocity at the aortic valve in angiotensin II treated mice versus mice receiving angiotensin II and leptin antagonist (LA).

Peak systolic velocity was decreased in AngII treated mice that also received LA application, vs. AngII alone (p=0.03, FIG. 21). Notably, since no aortic valve obstruction or changes in its annulus diameter were detected, the PSV parameter is likely reflecting the interaction between proximal aortic hemodynamics, and left ventricular systolic contraction. Thus, PSV moderation by LA may represent attenuation of both aortic and LV remodeling.

Figure 22:
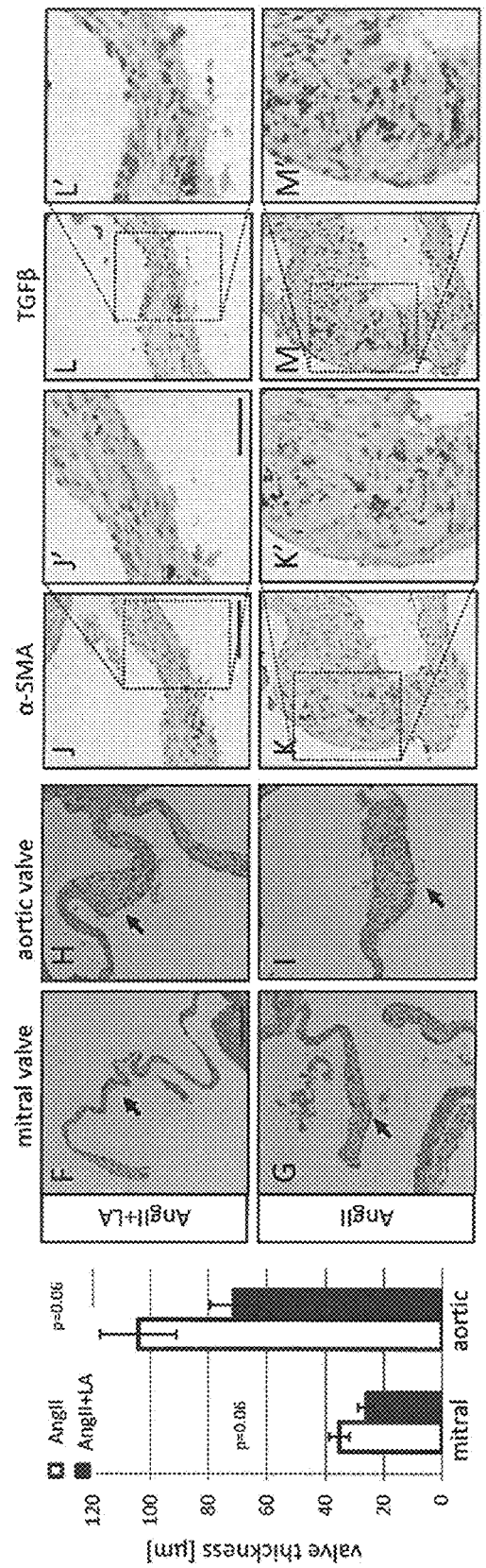
FIG. 22 illustrates aortic and mitral valve thickness (graph on left), and staining of valve leaflets with H&E (panels F-I). αSMA and TGFβ (panels J-M', staining for aortic valves) in mice receiving angiotensin II versus mice treated with angiotensin II and leptin antagonist (LA).

LA also attenuated remodeling of the LV valve. AngII-induced thickening of aortic and mitral valve leaflets was reduced by LA application in both valves (p=0.06 in both valves, FIG. 22 left panels F-I).

The αSMA and TGFβ antigens were observed in aortic valve leaflet stromal cells in all AngII treated mice (FIG. 22 panels J-M'); decreased proliferation of stromal cells in LA treated mice was demonstrated through Ki67 staining (p=0.26).

Thus, the present findings show that application of a leptin antagonist at the pivotal location on the proximal ascending aortic surface prevents rupture of thoracic aneurysms induced by systemic infusion of Ang II. Local inhibition of leptin activity reduces the degenerative effects of Ang II on the proximal aorta, which underlie aortic wall destabilization. Thus, moderation of Ang II induced aortic dilatation and attenuates left heart remodeling, presumably via the aorto-ventricular coupling.

These results highlight the role of leptin as a key mediator of Ang II signaling and indicate that leptin which underlie left ventricular hypertrophy also drives the formation of early aortic valve hyperplastic lesions, which may progress to aortic valve stenosis (AVS).

Example 3

The Role of Leptin in AVS

Materials and Methods

Human AVS and normal arterial valve (AV) samples were collected for analysis, including autopsy samples, freshly collected AVS specimens from patients undergoing aortic valve replacement surgery, and normal aortic valves from explanted hearts. Formalin fixed valve samples were analyzed by immunohistochemistry for leptin, leptin receptor, CD68 and αSMA. Fresh samples of AVS valves and normal aortic valves underwent total RNA extraction and analyzed by qPCR and Nanostring technique to assess leptin and leptin receptor mRNA levels. Retroperitoneal fat was used as a positive control in both assays.

Results

Figure 23:
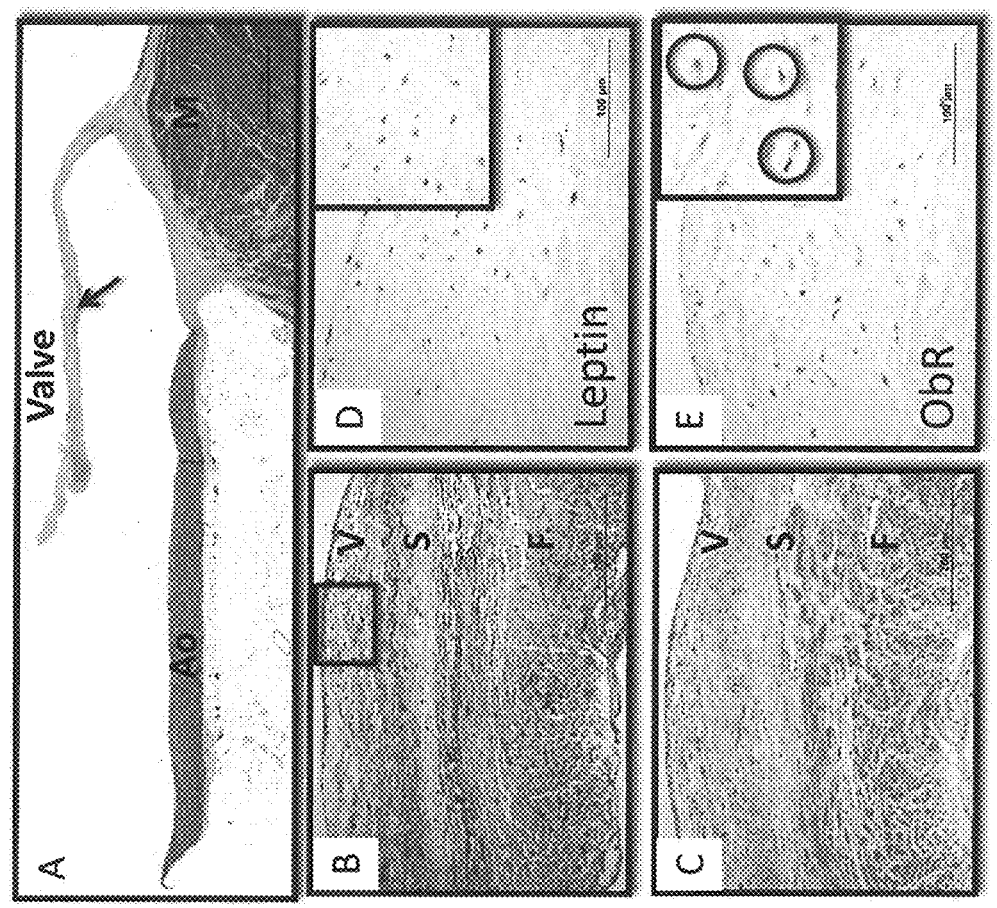
FIG. 23 illustrates expression of leptin (D), and leptin receptor (E) in normal human aortic valve leaflet tissue.
Figure 24:
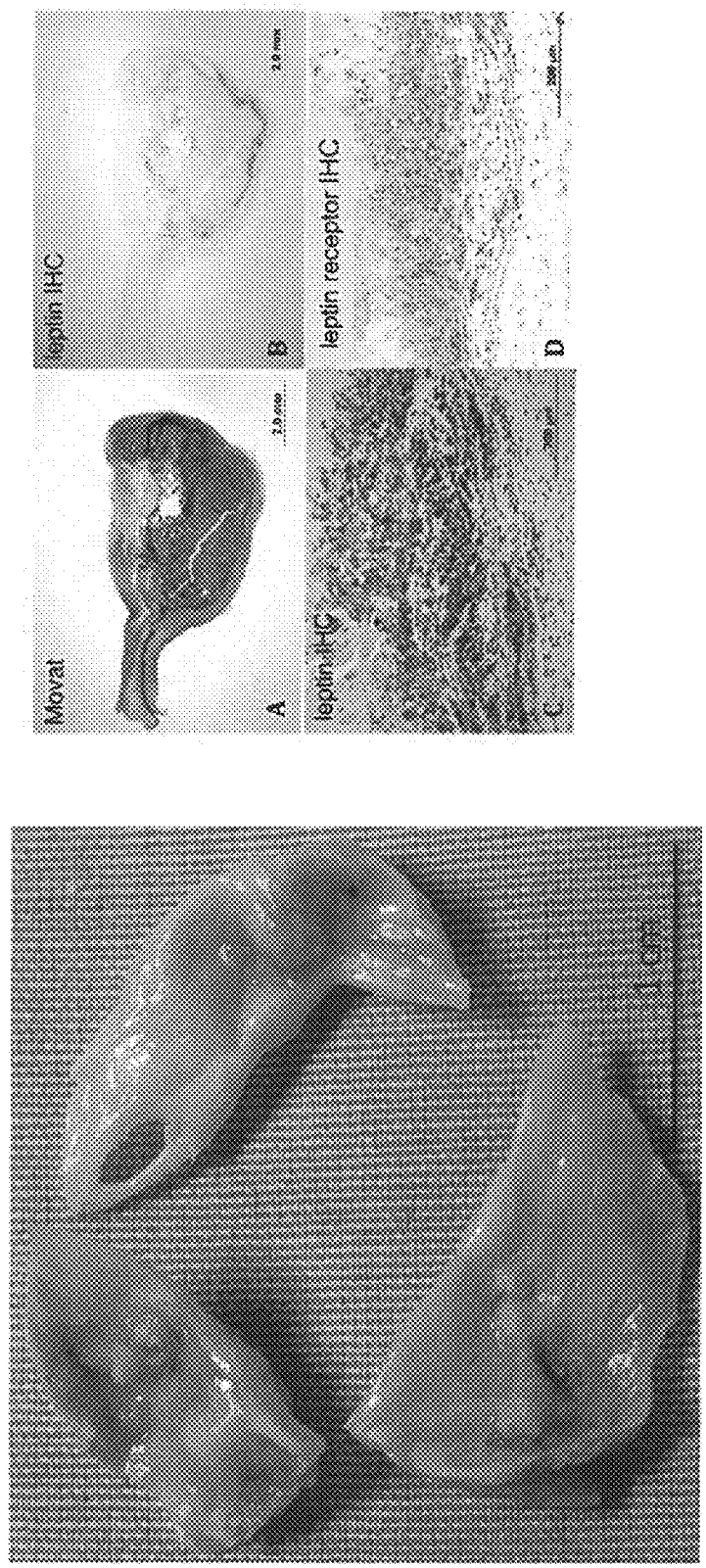
FIG. 24 Illustrates leptin and leptin receptor antigen prevalent in severe aortic valve stenosis, evident in SMC-like cells, and infiltrating macrophages.
Figure 25:
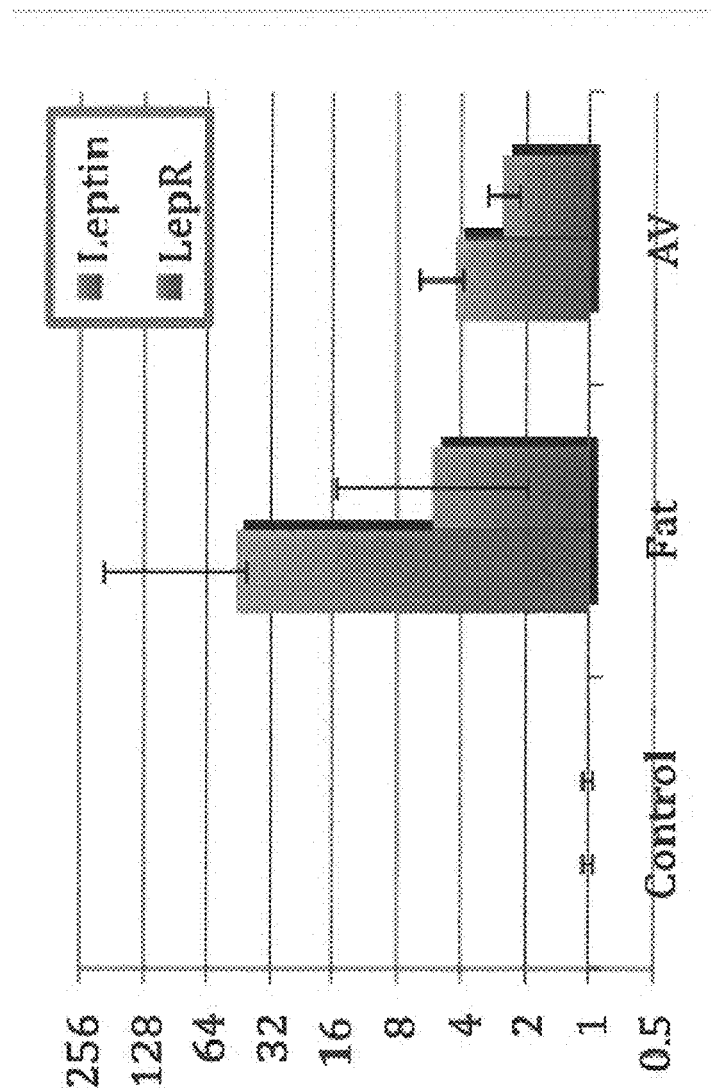
FIG. 25 illustrates leptin and leptin receptor mRNA levels in leaflets of stenosed aortic valve versus normal aortic valve controls, and fat tissue (as positive control).

Normal aortic valve leaflets lack leptin (Ob) antigen, and show very few leptin receptor (ObR) positive cells (FIG. 23). Advanced AVS disease was characterized by extensive ossification and infiltration of inflammatory macrophages in the non-calcified rim of cellular tissue (FIG. 24). Leptin was demonstrated mostly in two cell types, SMC-like elongated cells, and macrophage-like round cells, and its prevalence was proportional to the severity of AVS disease. In situ hybridization analysis performed on AVS samples demonstrated leptin mRNA expression, suggesting de novo synthesis (not shown) Leptin and leptin receptor mRNA levels were assessed by qPCR and Nanostrings hybridization, using total RNA extracted from freshly collected AVS. AVS were compared to noithal AV leaflets (FIG. 25), revealing increased leptin and leptin receptor mRNA in AVS samples.

Figure 26:
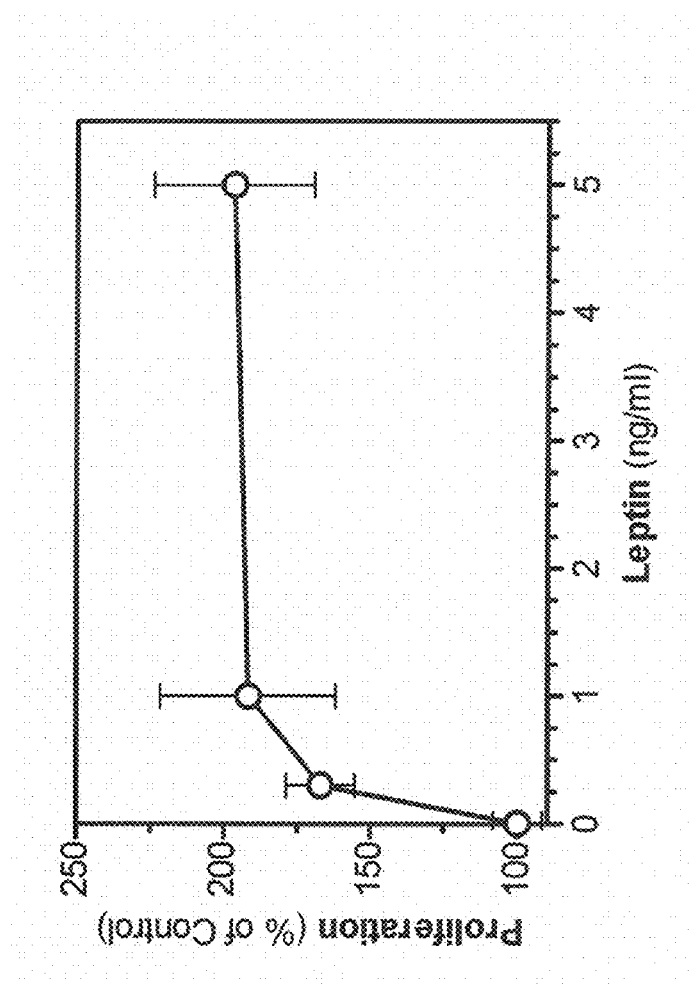
FIG. 26 illustrates proliferation of valve interstitial cells (VICs) in response to leptin stimulation.

To investigate the potential impact of AngII and leptin on human valve cells, in vitro analysis revealed that AngII-mediated proliferation of human valve interstitial cells (VICs) is leptin mediated (Leptin-induced proliferation of VICs in FIG. 26). This suggests that leptin synthesized in aortic valve leaflets by VICs and inflammatory macrophages may elicit VIC proliferation and subsequent ossification via a paracrine/autocrine pathways.

It is appreciated that certain features of the invention, which are, for clarity, described in the context of separate embodiments, may also be provided in combination in a single embodiment Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a cardiovascular disorder comprising:
locally administering a leptin antagonist to a cardiovascular tissue by a carrier configured for localized release of said leptin antagonist, for down-regulating an expression or activity of leptin in said cardiovascular tissue, said leptin antagonist is a superactive leptin antagonist peptide having the amino acid sequence of SEQ ID NO:1.

2. The method of claim 1, wherein said cardiovascular tissue is aortic and/or mitral heart valve leaflet tissue.

3. The method of claim 1, wherein said cardiovascular tissue is the inner (luminal surface) of an aorta.

4. The method of claim 1, wherein said cardiovascular tissue is arterial wall tissue.

5. The method of claim 1, wherein said cardiovascular disorder is a vascular aneurysm.

6. The method of claim 1, wherein said cardiovascular disorder is an aortic vascular disorder.

7. The method of claim 1, wherein said locally administrating is effected via an intravascular catheter.

8. The method of claim 1, wherein said cardiovascular disorder is left ventricular remodeling.

9. The method of claim 1, wherein locally administrating is effected via direct injection.

10. The method of claim 1, wherein said carrier is a scaffold for slow release and said cardiovascular tissue is the luminal surface of an aorta, and wherein said scaffold for slow release is applied to said luminal surface of the aorta via arterial catheterization.

11. The method of claim 10, wherein said scaffold is biodegradable matrix for slow sustained release.

12. The method of claim 7, wherein said locally administrating is effected intra-arterially.

* * * * *